(12) United States Patent
Alcaraz et al.

(10) Patent No.: US 6,720,452 B2
(45) Date of Patent: Apr. 13, 2004

(54) ADAMANTANE DERIVATIVES

(75) Inventors: Lilian Alcaraz, Loughborough (GB); Mark Furber, Loughborough (GB); Timothy Luker, Loughborough (GB); Michael Mortimore, Oxfordshire (GB); Philip Thorne, Loughborough (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/149,190

(22) PCT Filed: Dec. 1, 2000

(86) PCT No.: PCT/SE00/02418

§ 371 (c)(1),
(2), (4) Date: Jun. 10, 2002

(87) PCT Pub. No.: WO01/42194

PCT Pub. Date: Jun. 14, 2001

(65) Prior Publication Data

US 2002/0193414 A1 Dec. 19, 2002

(30) Foreign Application Priority Data

Dec. 9, 1999 (SE) .............................................. 9904505

(51) Int. Cl.$^7$ ..................... C07C 233/05; A61K 31/165
(52) U.S. Cl. ..................... 564/165; 564/157; 564/162; 564/163; 564/164; 564/168; 562/455; 548/336.1; 514/399; 514/400; 514/563; 514/616; 514/618; 514/619; 514/620
(58) Field of Search ................................. 564/157, 162, 564/163, 164, 165, 168; 514/563, 616, 618, 619, 620, 399, 400; 548/336.1; 562/455

(56) References Cited

U.S. PATENT DOCUMENTS

| 3,464,998 A | 9/1969 | Krimmel et al. |
| 3,732,305 A | 5/1973 | Bauer et al. |
| 3,789,072 A | 1/1974 | Bernstein |

FOREIGN PATENT DOCUMENTS

| EP | 0395093 A1 | 10/1990 |
| EP | 0564924 A2 | 10/1993 |
| WO | 95/04720 | 2/1995 |
| WO | 95/36047 | 11/1995 |
| WO | 95/32949 | 12/1995 |
| WO | 97/32882 | 9/1997 |
| WO | WO 99/29660 A1 | 6/1999 |
| WO | WO 99/29661 A1 | 6/1999 |
| WO | 99/29686 | 7/1999 |
| WO | WO 00/61569 A1 | 10/2000 |
| WO | 00/71529 A1 | 11/2000 |
| WO | 01/44170 A1 | 6/2001 |
| WO | 01/44213 A1 | 6/2001 |
| WO | 01/46200 A1 | 6/2001 |

OTHER PUBLICATIONS

Nomura et al., "Synthesis of Cyclic Imines Having Conjugated Exocyclic Double Bond", Bull. Chem. Soc. Jpn., 1983, vol. 56, p. 3199–3120.

Palucki et al., "Palladium–Catalyzed Intermolecular Carbon–Oxygen Bond Formation: A New Synthesis of Aryl Ethers", J. Am. Chem., 1997, vol. 119, pp. 3395–3396.

Smith et al., "Solid and Solution Phase Organic Syntheses of Oligomeric Thioureas", J. Org. Chem, 1996, vol. 61, pp. 8811–8818.

STN International, File CAPLUS, CAPLUS accession No. 1968:402562, Document No. 69:2562, Sasaki et al., "Synthesis of adamantane derivatives II. Preparation of some derivatives from adamantylacetric acid", Bull. Chem. Soc. Jap., 1968, 41(1), pp. 238–240.

STN International, File CAPLUS, CAPLUS accession No. 1974:26871, Document No. 80:28671, Danilenko et al., "Synthesis and biological activity of adamantane derivatives. II. N–(1–Adamantoyl)anthranilic acids", Kim.–Farm.Zh., 1973, 7(10), pp. 15–17.

STN International, File CAPLUS, CAPLUS accession No. 1975:3853, Document No. 82:3853, Kreutzberger et al., "Antiviral agents. 3. Aliphatic acid amide grouping as partial structure in virustatics", Arch. Pham., 1974, 307(10), pp. 766–774.

STN International, File CAPLUS, CAPLUS accession No. 1975:592744, Document No. 83:192744, Kreutzberger et al., "Antiviral agents. 4. Aromatically substituted carbonic acid amide structure in potentially virustatic compounds", Arzneim.–Forsch., 1975, 25(7) 994–997.

(List continued on next page.)

Primary Examiner—Shailendra Kumar
(74) Attorney, Agent, or Firm—Morgan, Lewis & Bockius LLP

(57) ABSTRACT

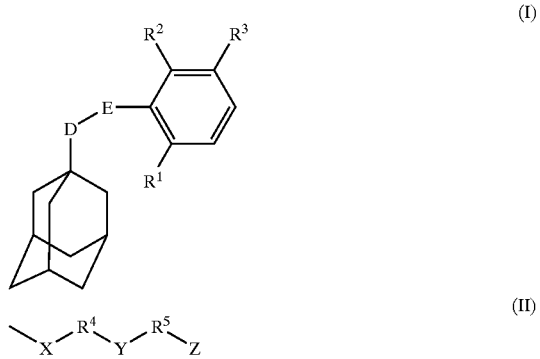

The invention provides adamantane derivatives of formula (I), a process for their preparation, pharmaceutical compositions containing them, a process for preparing the pharmaceutical compositions, and their use in therapy.

15 Claims, No Drawings

OTHER PUBLICATIONS

STN International, File CAPLUS, CAPLUS accession No. 1977:89560, Document No. 86:89560, Danilenko, G.I., et al., "Synthesis and biological activity of adamatane derivatives. VI. Antiinflammatory action of adamantylamides of pyridinecarboxylicacids"; Khim.–Famr.zh. (1976, 10(8), pp. 51–53.

STN International, File CAPLUS, CAPLUS accession No. 1996:344490, Document No. 125:115117, Kalindjian et al., "The Synthesis of radioligand with high potency and selectivity for CCKB/gastrain receptors", Bioorg. Med. Chem. Lett. 1996, 6(10), pp. 1171–1174.

STN International, File CAPLUS, CAPLUS accession No. 1997:390174, Document No. 127:95591, Gibson et al., "Incorporation of conformationally constrained phenylalanine derivatives Tic, Sic, Hic and Nic into a cholecystokinin–b/gastrin receptor antagonist", Bioorg. Med. Chem. Lett., 1997, 7(10), pp. 1289–1292.

Syamala et al., "Modification of Photochemical Reactivity by Cyclodextrin Complexation: Product Selectivity in Photo–Fries Rearrangement", Tetrahedron, vol. 44, No. 23, 1998, pp. 7234–7242.

Tsunoda et al., "1,1'–(Azodicarbonyl)dipiperidine–Tributylphosphine, A New Reagent System for Mitsunobu Reaction", Tetrahedron Letters, vol. 34, No. 10, 1993. pp. 1639–1642.

Wolfe et al., "An Improved Catalyst System for Aromatic Carbon—Nitrogen Bond Formation: The Possible Involvement of Bis(Phosphine) Palladium Complexes as Key Intermediates", J. Am. Chem. Soc., 1996, vol. 118, pp. 7215–7216.

Zeng et al., "Design of New Topoisomerase II Inhibitors Based upon a Quinobenzoxazine Self–Assembly Model", J. Med. Chem., 199, vol. 41, pp. 4273–4278.

Billotte, "Synthesis of C–Substituted Cyclic Amines Using Azacycloalkyl Organozinc Reagents", Syn. Lett., 1998, pp. 379–380.

Chemical Abstracts, vol. 82, No. 3, Jan. 20, 1975, No et al., "Tetrakis(1–adamantyacetoxy)silane in organic synthesis", Abstract No. 16510v. p. 469, Zh. Obshch. Kim. 1974, 44 (10), 2359.

Chemical Abstracts, vol. 84, No. 9, Mar. 1, 1976, p. 527, The Abstract No. 59466u, JP 75108264A (Maruyama, Isamu et al.) Aug. 26, 1975.

Chemical Abstracts, vol. 86, No. 17, Apr. 25, 1977, Danilenko et al., "Synthesis and biological activity of adamantane derivatives. V. Virus–inhibiting effect of arylamides of adamantanecarboxylic acids", p. 505, Abstract No. 120855e, Khim.–Farmm.Zh. 1976. 10(7), pp. 60–62.

Claxton et al., "2,3,4,5–Tetrahydropyridine", Org. Synth. 1977, vol. 56, pp. 118–122.

Liverton et al., "Design and Synthesis of Potent, Selective, and Orally Bioavailable Tetrasubstituted Imidazole Inhibitors of p38 Mitogen–Activated Protein Kinase", J. Med. Chem., 1999, vol. 42, pp. 2180–2190.

Narayanan, "Adamantyl Analogs of 2–(3–Dimethylaminopropylthio)cinnamanilide", Journal of Medicinal Chemistry, vol. 15, No. 11, pp. 1180–1182, 1972.

ADAMANTANE DERIVATIVES

This application is a 371 of PCT/SE00/02418, filed Dec. 1, 2000.

The present invention relates to adamantane derivatives, a process for their preparation, pharmaceutical compositions containing them, a process for preparing the pharmaceutical compositions, and their use in therapy.

The $P2X_7$ receptor (previously known as P2Z receptor), which is a ligand-gated ion channel, is present on a variety of cell types, largely those known to be involved in the inflammatory/immune process, specifically, macrophages, mast cells and lymphocytes (T and B). Activation of the $P2X_7$ receptor by extracellular nucleotides, in particular adenosine triphosphate, leads to the release of interleukin-1β (IL-1β) and giant cell formation (macrophages/microglial cells), degranulation (mast cells) and L-selectin shedding (lymphocytes). $P2X_7$ receptors are also located on antigen-presenting cells (APC), keratinocytes, salivary acinar cells (parotid cells), hepatocytes, erythrocytes, erydiroleukaemic cells, monocytes, fibroblasts, bone marrow cells, neurones and renal mesangial cells.

It would be desirable to make compounds effective as $P2X_7$ receptor antagonists for use in the treatment of inflammatory, immune or cardiovascular diseases, in the aetiologies of which the $P2X_7$ receptor may play a role.

In accordance with the present invention, there is therefore provided a compound of general formula

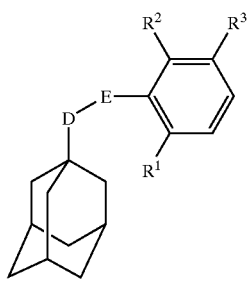

(I)

wherein D represents $CH_2$ or $CH_2CH_2$, preferably $CH_2$;

E represents C(O)NH or, preferably, NHC(O);

$R^1$ and $R^2$ each independently represent a hydrogen or halogen (e.g. fluorine, chlorine, bromine or iodine) atom, or an amino ($NH_2$), nitro ($NO_2$), $C_1$–$C_6$ alkyl or trifluoromethyl group;

$R^3$ group of formula

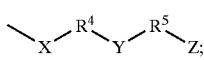

(II)

X represents an oxygen or sulphur atom or a group NH, SO or $SO_2$;

Y represents an oxygen or sulphur atom or a group $NR^{11}$, SO or $SO_2$;

Z represents a group —OH, —SH, —$CO_2H$, $C_1$–$C_6$ alkoxy, $C_1$–$C_6$ alkylthio, $C_1$–$C_6$-alkylsulphinyl, $C_1$–$C_6$-alkylsulphonyl, —$NR^6R^7$, —$C(O)NR^8R^9$, imidazolyl, 1-methylimidazolyl, —$N(R^{10})C(O)$—$C_1$–$C_6$ alkyl, $C_1$–$C_6$ alkylcarbonyloxy, $C_1$–$C_6$ alkoxycarbonyloxy, —$OC(O)NR^{12}R^{13}$, —$OCH_2OC(O)R^{14}$, —$OCH_2OC(O)OR^{15}$ or —$OC(O)OCH_2OR^{16}$;

$R^4$ represents a linear or branched $C_2$–$C_6$ alkylene group;

$R^5$ represents a linear or branched $C_1$–$C_6$ alkylene group;

$R^6$, $R^7$, $R^8$, $R^9$, $R^{10}$, $R^{12}$ and $R^{13}$ each independently represent a hydrogen atom, or a $C_1$–$C_6$ alkyl group optionally substituted by at least one hydroxyl group (e.g., one, two or three hydroxyl groups);

$R^{11}$ represents a hydrogen atom, or a $C_1$–$C_6$ alkyl group optionally substituted by at least one substituent (e.g. one, two or three substituents) independently selected from hydroxyl and $C_1$–$C_6$ alkoxy; and $R^{14}$, $R^{15}$ and $R^{16}$ each independently represent a $C_1$–$C_6$ alkyl group; with the provisos that (i) when E represents NHC(O), X represents O, S or NH and Y represents O, then Z represents —$NR^6R^7$ where $R^6$ represents a hydrogen atom and $R^7$ represents either a hydrogen atom or a $C_1$–$C_6$ alkyl group substituted by at least one hydroxyl group, and (ii) when E represents NHC(O), X represents O, S or NH, Y represents NH and $R^5$ represents $CH_2CH_2$, then Z is not —OH or imidazolyl; or a pharmaceutically acceptable salt or solvate thereof.

In the context of the present specification, unless otherwise indicated, an alkyl substituent or alkyl moiety in a substituent group may be linear or branched. In the present invention, an alkyl group or moiety may contain up to 6 carbon atoms, examples of which include methyl, ethyl, n-propyl, isopropyl, n-butyl, isobutyl, t-butyl, n-pentyl and n-hexyl.

Preferably, $R^1$ and $R^2$ each independently represent a hydrogen or halogen atom, or an amino, nitro, $C_1$–$C_4$ alkyl or trifluoromethyl group.

More preferably, $R^1$ and $R^2$ each independently represent a hydrogen, chlorine or bromine atom, or an amino, nitro, $C_1$–$C_3$ alkyl or trifluoromethyl group.

Most preferably, $R^1$ and $R_2$ each independently represent a hydrogen or chlorine atom.

Preferably X represents an oxygen atom or a group NH.

Preferably Z represents a group —OH, —SH, —$CO_2H$, $C_1$–$C_4$ alkoxy, $C_1$–$C_4$ alkylthio, $C_1$–$C_4$-alkylsulphinyl, $C_1$–$C_4$-alkylsulphonyl, —$NR^6R^7$, —$C(O)NR^8R^9$, imidazolyl, 1-methylimidazolyl, —$N(R^{10})C(O)$—$C_1$–$C_4$ alkyl, $C_{1-C4}$ alkylcarbonyloxy, $C_1$–$C_4$ alkoxycarbonyloxy, —$OC(O)NR^{12}R^{13}$, —$OCH_2OC(O)R^{14}$, —$OCH_2OC(O)OR^{15}$ or —$OC(O)OCH_2OR^{16}$.

Particularly preferred groups Z include —OH, —$CO_2H$, methoxy, methylthio, methylsulphinyl, methylsulphonyl, —$NR^6R^7$, —$C(O)NR^8R^9$, —$N(R^{10})C(O)CH_3$, imidazolyl, 1-methylimidazolyl, $C_1$–$C_4$ alkylcarbonyloxy, $C_1$–$C_4$ alkoxycarbonyloxy, —$OC(O)NR^{12}R^{13}$, —$OCH_2OC(O)R^{14}$, —$OCH_2OC(O)OR^{15}$ and —$OC(O)OCH_2OR^{16}$.

$R^4$ preferably represents a $C_2$–$C_4$ alkyl group, for example a linear alkyl group such as —$(CH_2)_2$— or —$(CH_2)_3$—.

$R^5$ preferably represents a $C_1$–$C_5$ alkyl group, for example —$CH_2$—, —$(CH_2)_2$—, —$(CH_2)_3$—, —$CH_2CH(CH_3)$—, —$CH(CH_3)CH_2$—, —$(CH_2)_2C(CH_3)_2$— or —$CH_2C(CH_3)_2$—.

Preferably $R^6$, $R^7$, $R^8$, $R^9$, $R^{10}$, $R^{12}$ and $R^{13}$ each independently represent a hydrogen atom, or a $C_1$–$C_4$ alkyl group optionally substituted by at least one hydroxyl group.

Y is conveniently a group $NR^{11}$. It is preferred that $R^{11}$ represents a hydrogen atom, or a $C_1$–$C_4$ alkyl group optionally substituted by at least one substituent independently selected from hydroxyl and $C_1$–$C_6$, preferably $C_1$–$C_4$, alkoxy.

$R^{14}$, $R^{15}$ and $R^{16}$ each independently represent a $C_1$–$C_6$ alkyl group, preferably a $C_1$–$C_4$ alkyl group.

Preferred compounds of the invention include:

2-Chloro-5-[2-(2-methoxyethylamino)ethylamino]-N-(tricyclo[3.3.1.1³,⁷]dec-1-ylmethyl)-benzamide, hydrochloride,

[2-[4-Chloro-3-(tricyclo[3.3.1.1³,⁷]dec-1-ylmethyl) carbamoyl-phenylamino]-ethyamino]-acetic acid, hydrochloride, 2-Chloro-5-[3-(3-hydroxy-propylamino)-propoxy]-N-(tricyclo[3.3.1.1³,⁷]dec-1-ylmethyl)-benzamide, hydrochloride, 2-Chloro-5-[2-(3-hydroxypropylamino)ethylamino]-N-(tricyclo[3.3.1.1³,⁷]dec-1-ylmethyl)-benzamide, acetate, 5-[2-(2-Aminoethylamino)ethylamino]-2-chloro-N-(tricyclo[3.3.1.1³,⁷]dec-1-ylmethyl)-benzamide, acetate, 5-[2-(2-Acetylaminoethylamino)ethylamino]-2-chloro-N-(tricyclo[3.3.1.1³,⁷]dec-1-ylmethyl)-benzamide, acetate,

[2-[4-Chloro-3-(tricyclo[3.3.1.1³,⁷]dec-1-ylmethyl) carbamoyl-phenylamino]-ethylamino]-propionic acid, 2-Chloro-5-[2-(2-methylcarbamoylethylamino) ethylamino]-N-(tricyclo[3.3.1.1³,⁷]dec-1-ylmethyl)-benzamide, acetate, 2-Chloro-5-[2-(2-dimethylcarbamoylethylamino) ethylamino]-N-(tricyclo[3.3.1.1³,⁷]dec-1-ylmethyl)-benzamide, acetate, 2-Chloro-5-[3-(3-hydroxypropylthio)propoxy]-N-(tricyclo[3.3.1.1³,⁷]dec-1-ylmethyl)-benzamide, 5-[2-(2-Aminoethylthio)ethoxy]-2-chloro-N-(tricyclo[3.3.1.1³,⁷]dec-1-ylmethyl)-benzamide, hydrochloride, 2-Chloro-5-[2-(3-hydroxypropylamino)ethoxy]-N-(tricyclo[3.3.1.1³,⁷]dec-1-ylmethyl)-benzamide, hydrochloride, 2-Chloro-5-[3-(3-hydroxypropylsulfonyl)propoxy]-N-(tricyclo[3.3.1.1³,⁷]dec-1-ylmethyl)-benzamide, (±)-2-Chloro-5-[3-(3-hydroxypropylsulfinyl)propoxy]-N-(tricyclo[3.3.1.1³,⁷]dec-1-ylmethyl)-benzamide, 2-Chloro-5-[2-(3-hydroxypropylthio)ethoxy]-N-(tricyclo[3.3.1.1³,⁷]dec-1-ylmethyl)-benzamide, (S)-2-Chloro-5-[2-(2-hydroxypropylamino)ethoxy]-N-(tricyclo[3.3.1.1³,⁷]dec-1-ylmethyl)-benzamide, hydrochloride, (R)-2-Chloro-5-[2-(2-hydroxypropylamino)ethoxy]-N-(tricyclo[3.3.1.1³,⁷]dec-1-ylmethyl)-benzamide, hydrochloride, (S)-2-Chloro-5-[2-(2-hydroxy-1-methylethylamino) ethoxy]-N-(tricyclo[3.3.1.1³,⁷]dec-1-ylmethyl)-benzamide, hydrochloride, (R)-2-Chloro-5-[2-(2-hydroxy-1-methylethylamino) ethoxy]-N-(tricyclo[3.3.1.1³,⁷]dec-1-ylmethyl)-benzamide, hydrochloride, (±)-2-Chloro-5-[2-(3-hydroxypropylsulfinyl)ethoxy]-N-(tricyclo[3.3.1.1³,⁷]dec-1-ylmethyl)-benzamide, 2-Chloro-5-[2-(3-hydroxypropylsulfonyl)ethoxy]-N-(tricyclo[3.3.1.1³,⁷]dec-1-ylmethyl)-benzamide, (±)-5-[2-(2-Aminoethylsulfinyl)ethoxy]-2-chloro-N-(tricyclo[3.3.1.1³,⁷]dec-1-ylmethyl)-benzamide, hydrochloride, 5-[2-(2-Aminoethylsulfonyl)ethoxy]-2-chloro-N-(tricyclo[3.3.1.1³,⁷]dec-1-ylmethyl)-benzamide, hydrochloride, 5-[3-(2-Aminoethylthio)propoxy]-2-chloro-N-(tricyclo[3.3.1.1³,⁷]dec-1-ylmethyl)-benzamide, hydrochloride, (±)-5-[3-(2-Aminoethylsulfinyl)propoxy]-2-chloro-N-(tricyclo[3.3.1.1³,⁷]dec-1-ylmethyl)-benzamide, hydrochloride, 5-[3-(2-Aminoethylsulfonyl)propoxy]-2-chloro-N-(tricyclo[3.3.1.1³,⁷]dec-1-ylmethyl)-benzamide, hydrochloride, 2-Chloro-5-[[2-[(3-hydroxy-3-methylbutyl)amino]ethyl] amino]-N-(tricyclo[3.3.1.1³,⁷]dec-1-ylmethyl)-benzamide, 2-Chloro-5-[2-[2-[(2-hydroxyethyl)amino]ethoxy]ethoxy]-N-(tricyclo[3.3.1.1³,⁷]dec-1-ylmethyl)-benzamide, hydrochloride, 2-Chloro-5-[[2-[[2-(methylthio)ethyl]amino]ethyl]amino]-N-(tricyclo[3.3.1.1³,⁷]dec-1-ylmethyl)-benzamide, 2-Chloro-5-[[2-[[2-(methylsulfinyl)ethyl]amino]ethyl] amino]-N-(tricyclo[3.3.1.1³,⁷]dec-1-ylmethyl)-benzamide, acetic acid salt, 2-Chloro-5-[2-[(2-hydroxy-2-methylpropyl)amino]ethoxy]-N-(tricyclo[3.3.1.1³,⁷]dec-1-ylmethyl)benzamide, dihydrochloride, 2-Chloro-5-[[2-[[2-(1-methyl-1H-imidazol-5-yl)ethyl] amino]ethyl]amino]-N-(tricyclo[3.3.1.1³,⁷]dec-1-ylmethyl)-benzamide, 2-Chloro-5-[[2-[[2-(1-methyl-1H-imidazol-4-yl)ethyl] amino)ethyl]amino]-N-(tricyclo[3.3.1.1³,⁷]dec-1-ylmethyl)-benzamide, and 2-Chloro-5-[[2-[[3-(1H-imidazol-1-yl)propyl]amino]ethyl] amino]-N-(tricyclo[3.3.1.1³,⁷]dec-1-ylmethyl)-benzamide.

The present invention further provides a process for the preparation of a compound of formula (I) as defined above which comprises:

a) when Y represents an oxygen or sulphur atom or a group $NR^{11}$, reacting a compound of general formula

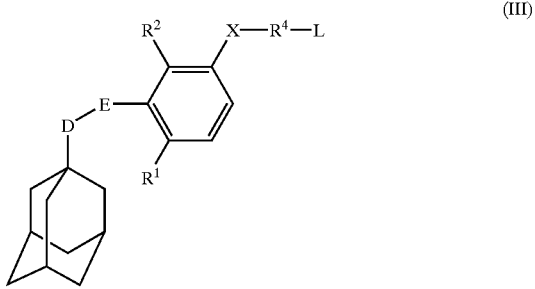

(III)

wherein L represents a leaving group (e.g. a halogen atom) and D, E, $R^1$, $R^2$, X and $R^4$ are as defined in formula (I), with a compound of general formula

(IV)

wherein $R^{20}$ represents —OH, —SH or —$NHR^{11}$ and $R^5$, $R^{11}$ and Z are as defined in formula (I); or b) when Y represents SO or $SO_2$, reacting a corresponding compound of formula (I) in which Y represents a sulphur atom with a suitable oxidising agent;

and optionally after (a) or (b) converting the compound of formula (I) obtained to a pharmaceutically acceptable salt or solvate thereof.

The processes of the invention may conveniently be carried out in a solvent, e.g. an organic solvent such as dichloromethane, tetrahydrofuran, or an alcohol such a ethanol, isopropanol or butanol, at a temperature, e.g. in the range from 0 to 200° C., preferably in the range from 0 to 150° C. The oxidising agent used in (b) above may, for example, be 3-chloroperoxybenzoic acid or potassium peroxymonosulphate, commercially sold under the trade mark "OXONE".

Compounds of formula (III) are either known in the art, e.g. from WO 99/29660 and WO 99/29661 or may be prepared easily using known techniques. Compounds of formula (III) wherein X is an oxygen atom can be prepared from the corresponding phenol (WO 99/29660 and WO 99/29661) and a haloalkanol such as 2-chloroethanol, 3-chloropropanol or 4-chlorobutanol in the presence of triphenylphosphine and diethyl azodicarboxylate. Compounds of formula (III) wherein X is an NH group can be prepared from the corresponding aniline (WO 99/29660 and WO 99/29661) and a haloalkanal such as chloroacetaldehyde, 4-chlorobutanal, 5-chloropentanal or an appropriately protected hydroxyalkanal such as 3-tert-butyldimethylsilyloxypropanal in the presence of a reducing agent such as sodium triacetoxyborohydride. In the latter case, removal of the protecting group and activation, for example by conversion into the mesylate group affords compounds of formula (III). Compounds of formula (III) wherein X is a sulfur atom can be prepared from the corresponding thiophenol in the presence of a dihaloalkane such as 1-bromo-2-chloroethane, 1-bromo-3-chloropropane or 1-bromo-4-chlorobutane in the presence of a base such as cesium carbonate.

Compounds of formula (IV) are either commercially available, are well known in the literature or may be prepared easily using known techniques.

It will be appreciated by those skilled in the art that in the processes of the present invention certain functional groups such as hydroxyl, carboxyl or amino groups in the starting reagents or intermediate compounds may need to be protected by protecting groups. Thus, the preparation of the compounds of formula (I) may involve at a certain stage the removal of one or more protecting groups.

The protection and deprotection of functional groups is described in 'Protective Groups in Organic Chemistry', edited by J. W. F. McOmie, Plenum Press (1973) and 'Protective Groups in Organic Synthesis', 2nd edition, T. W. Greene and P. G. M. Wuts, Wiley-Interscience (1991).

The compounds of formula (I) above may be converted to a pharmaceutically acceptable salt or solvate thereof, preferably an acid addition salt such as a hydrochloride, hydrobromide, phosphate, acetate, fumarate, maleate, tartrate, citrate, oxalate, methanesulphonate or p-toluenesulphonate, or an alkali metal salt such as a sodium or potassium salt.

Certain compounds of formula (I) are capable of existing in stereoisomeric forms. It will be understood that the invention encompasses all geometric and optical isomers of the compounds of formula (I) and mixtures thereof including racemates. Tautomers and mixtures thereof also form an aspect of the present invention.

The compounds of the present invention are advantageous in that they possess pharmacological activity and have utility as modulators of $P2X_7$ receptor activity. They are therefore indicated as pharmaceuticals for use in the treatment or prevention of rheumatoid arthritis, osteoarthritis, psoriasis, allergic dermatitis, asthma, hyperresponsiveness of the airway, chronic obstructive pulmonary disease (COPD), bronchitis, septic shock, glomerulonephritis, irritable bowel disease, Crohn's disease, ulcerative colitis, atherosclerosis, growth and metastases of malignant cells, myoblastic leukaemia, diabetes, neurodegenerative disease, Alzheimer's disease, meningitis, osteoporosis, burn injury, ischaemic heart disease, stroke, peripheral vascular disease and varicose veins.

Accordingly, the present invention provides a compound of formula (I), or a pharmaceutically acceptable salt or solvate thereof, as hereinbefore defined for use in therapy.

In another aspect, the invention provides the use of a compound of formula (I), or a pharmaceutically acceptable salt or solvate thereof, as hereinbefore defined in the manufacture of a medicament for use in therapy.

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

The invention further provides a method of effecting immunosuppression (e.g. in the treatment of rheumatoid arthritis, iritable bowel disease, atherosclerosis, psoriasis, pulmonary disease, e.g. COPD or bronchitis, or diseases of the central nervous system, e.g. Alzheimer's disease or stroke) which comprises administering a therapeutically effective amount of a compound of formula (I), or a pharmaceutically acceptable salt or solvate thereof, as hereinbefore defined to a patient.

For the above-mentioned therapeutic uses the dosage administered will, of course, vary with the compound employed, the mode of administration, the treatment desired and the disease or condition indicated. For effecting immunosuppression, the daily dosage of the compound of formula (I) will typically be in the range from 0.001 mg/kg to 30 mg/kg.

The compounds of formula (I) and pharmaceutically acceptable salts and solvates thereof may be used on their own but will generally be administered in the form of a pharmaceutical composition in which the formula (I) compound/salt/solvate (active ingredient) is in association with a pharmaceutically acceptable adjuvant, diluent or carrier. Depending on the mode of administration, the pharmaceutical composition will preferably comprise from 0.05 to 99%w (percent by weight), more preferably from 0.10 to 70%w, of active ingredient, and, from 1 to 99.95%w, more preferably from 30 to 99.90%w, of a pharmaceutically acceptable adjuvant, diluent or carrier, all percentages by weight being based on total composition.

Thus, the present invention also provides a pharmaceutical composition comprising a compound of formula (I), or a pharmaceutically acceptable salt or solvate thereof, as hereinbefore defined in association with a pharmaceutically acceptable adjuvant, diluent or carrier.

The invention further provides a process for the preparation of a pharmaceutical composition of the invention which comprises mixing a compound of formula (I), or a pharmaceutically acceptable salt or solvate thereof, as hereinbefore defined with a pharmaceutically acceptable adjuvant, diluent or carrier.

The pharmaceutical composition of the invention may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or suspensions, or by subcutaneous administration or by rectal administration in the form of suppositories or transdermally.

The present invention will now be further explained by reference to the following illustrative examples.

EXAMPLE 1

2-Chloro-5-[2-(2-methoxyethylamino)ethylamino]-N-(tricyclo[3.3.1.1³,⁷]dec-1-ylmethyl)-benzamide, hydrochloride

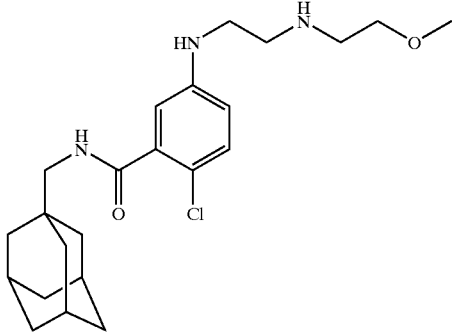

To a solution of 2-chloro-5-(2-chloroethylamino)-N-(tricyclo[3.3.1.1³,⁷]dec-1-ylmethyl)-benzamide (WO 99/29661) (0.2 g) and N,N-diisopropylethylamine (0.27 ml) in ethanol (5 ml) was added sodium iodide (0.08 g) and 2-methoxyethylamine (0.11 g). The reaction vessel was sealed and the reaction mixture heated at 90° C. for 15 h before concentration under reduced pressure. The residue was partitioned between ethyl acetate and sodium hydrogencarbonate solution, and the aqueous phase extracted with additional ethyl acetate. The combined organic phases were dried (MgSO₄) and concentrated under reduced pressure. The residue was purified by NPHPLC (eluting with 0–25% ethanol in dichloromethane) to afford 5-(N-(2-methoxyethyl)-2-aminoethyl)amino-2-chloro-N-(tricyclo[3.3.1.1³,⁷]dec-1-ylmethyl)-benzamide as a semi-solid. This was converted to the hydrochloride salt by stirring with 4M HCl in dioxane and concentrated under reduced pressure to leave the title compound as a white solid (0.085 g).

MS (APCI+ve) 420/422 (M+H)⁺

¹H NMR (CD₃OD) δ8.27 (1H, t); 7.20(1H, d); 7.73 (2H, m); 3.63 (2H, t); 3.46 (2H, t); 3.40 (3H, s); 3.26 (2H, m); 3.04 (2H, d); 1.98 (3H, s); 1.77 (3H, d); 1.67 (3H, d); 1.62 (6H, s).

EXAMPLE 2

[2-[4-Chloro-3-(tricyclo[3.3.1.1³,⁷]dec-1-ylmethyl)carbamoyl-phenylamino]-ethylamino]-acetic Acid, hydrochloride

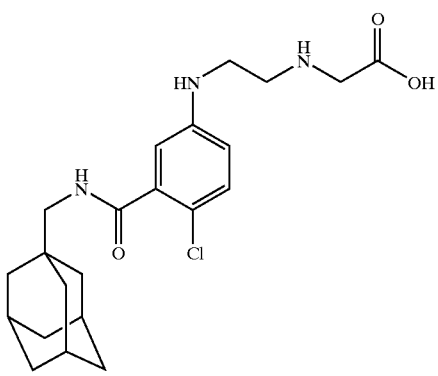

a) [2-[4-Chloro-3-(tricyclo[3.3.1.1³,⁷]dec-1-ylmethyl)carbamoyl-phenylamino]-ethylamino]-acetic Acid, 1,1-dimethylethyl ester Prepared according to the method of Example 1 using 2-chloro-5-(2-chloroethyl)amino-N-(tricyclo[3.3.1.1³,⁷]dec-1-ylmethyl)-benzamide (WO 99/29661) (0.2 g) and tertbutyl glycine (0.26 g) to deliver the sub-title compound as a brown foam (0.10 g).

¹H NMR (CD₃OD) δ7.13 (1H, d); 6.66 (2H, m); 3.20 (2H, t); 3.02 (2H, s); 2.79 (2H, t); 1.97 (3H, s); 1.76 (3H, d); 1.72 (3H, d); 1.61 (6H, s); 1.43 (9H, s).

b) [2-[4-Chloro-3-(tricyclo[3.3.1.1³,⁷]dec-1-ylmethyl)carbamoyl-phenylamino]-ethylamino]-acetic Acid, hydrochloride To [2-[4-chloro-3-(tricyclo[3.3.1.1³,⁷]dec-1-ylmethyl)carbamoyl-phenylamino]-ethylamino]-acetic acid, 1,1-dimethylethyl ester (0.10 g, Example 2a) was added a solution of HCl in dioxane (5 ml of a 4M solution) and reaction mixture stirred at room temperature for 48 h before concentration under reduced pressure. The residue was recrystallised twice from propan-2-ol/ethyl acetate/ether mixture to afford the title compound as a white solid (0.006 g).

¹H NMR (CD₃OD) δ8.30 (1H, t); 7.20 (1H, d); 6.72 (2H, m); 3.94 (2H, s); 3.47 (2H, s); 3.28 (2H, m); 3.03 (2H, s); 1.97 (3H, s); 1.76 (3H, d); 1.68 (3H, d); 1.61 (6H, s).

EXAMPLE 3

2-Chloro-5-[3-(3-hydroxy-propylamino)-propoxy]-N-(tricyclo[3.3.1.1³,⁷]dec-1-ylmethyl)-benzamide, hydrochloride

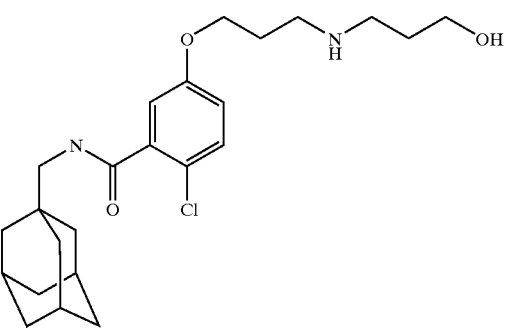

a) 2-Chloro-5-[3-chloropropoxy]-N-(tricyclo[3.3.1.1³,⁷]dec-1-ylmethyl)-benzamide To a solution of 2-chloro-5-hydroxy-N-(tricyclo[3.3.1.1³,⁷]dec-1-ylmethyl)-benzamide (WO 99/29661) (0.48 g) in ethanol (5 ml) was added caesium carbonate (0.977 g) and reaction mixture heated at 85° C. for 10 min. before addition of 1-bromo-3-chloropropane (0.74 ml). Heating was continued for 24 h before cooling to room temperature and concentration under reduced pressure. The residue was dissolved in ethyl acetate and washed with water(twice), then with KHSO₄ solution and brine. The organics were dried (MgSO₄), concentrated and the residue purified by silica gel chromatography (eluting with 20% ethyl acetate in isohexanes) to deliver the sub-title compound as a pale yellow foam (0.50 g).

¹H NMR (CDCl₃) δ7.28 (2H, m); 6.91 (1H, m); 6.34 (1H, t); 4.13 (2H, t); 3.73 (2H, t); 3.58 (2H, d); 2.23 (2H, tt); 2.10 (2H, d); 1.73 (3H, d); 1.65 (3H, d); 1.59 (6H, s).

b) 2-Chloro-5-[3-(3-hydroxy-propylamino)-propoxy]-N-(tricyclo[3.3.1.1$^{3,7}$]dec-1-ylmethyl)-benzamide, hydrochloride To a solution of 2-chloro-5-[3-chloropropoxy]-N-(tricyclo[3.3.1.1$^{3,7}$]dec-1-ylmethyl)-benzamide (0.25 g, Example 3a) and N,N-diisopropylethylamine (0.54 ml) in ethanol (5 ml) was added sodium iodide (0.08 g) and 1-propanolamine (0.24 ml). The reaction vessel was sealed and reaction mixture heated at 120° C. for 24 h. The reaction mixture was then concentrated under reduced pressure. The residue was partitioned between ethyl acetate and sodium hydrogencarbonate solution, and the aqueous phase extracted with additional ethyl acetate. The combined organic phases were dried (MgSO$_4$) and concentrated under reduced pressure. The residue was purified by NPHPLC (eluting with 0–25% ethanol in dichloromethane) to give 2-chloro-5-[3-(3-hydroxy-propylamino)-propoxy]-N-(tricyclo[3.3.1.1$^{3,7}$]dec-1-ylmethyl)-benzamide as a semi-solid. This compound was converted to the hydrochloride salt by stirring with 4M HCl in dioxane and concentrated under reduced pressure to leave the title compound as a white solid (0.036 g).

MS (APCI+ve) 435/437 (M+H)+

$^1$H NMR (CD$_3$OD) δ8.28 (1H, t); 7.27 (1H, d); 6.93 (2H, m); 4.05 (2H, t); 3.62 (2H, t); 3.15 (2H, m); 3.09 (2H, t); 2.96 (2H, m); 2.10 (2H, tt); 1.89 (3H, s); 1.82 (2H, tt); 1.68 (3H, d); 1.59 (3H, d); 1.53 (6H, s).

EXAMPLE 4

2-Chloro-5-[2-(3-hydroxypropylamino)ethylamino]-N-(tricyclo[3.3.1.1$^{3,7}$]dec-1-ylmethyl)-benzamide, acetate

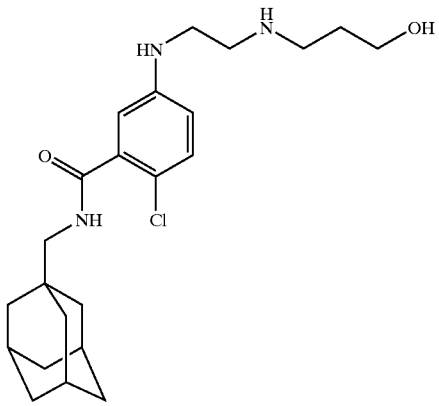

To a solution of 2-chloro-5-(2-chloroethylamino)-N-(tricyclo[3.3.1.1$^{3,7}$]dec-1-ylmethyl)-benzamide (WO 99/29661) (0.2 g) and N,N-diisopropylethylamine (0.5 ml) in 1-butanol (10 ml) was added sodium iodide (0.08 g) and 3-aminopropan-1-ol (0.12 g). The reaction vessel was sealed and the reaction mixture heated at 110° C. for 15 h before being concentrated under reduced pressure. The residue was purified by silica gel chromatography (eluting with of 0–100% ethanol in dichloromethane with 1% triethylamine), and further purified by RPHPLC (eluting with 15–95% MeCN in 0.1% AcONH$_4$ aqueous), to afford the title compound as a solid (0.035 g).

MS (APCI+ve) 376/378 (M+H)+

$^1$H NMR (CDCl$_3$) δ7.12 (1H, d); 6.88 (1H, d); 6.58 (1H, dd); 6.52 (1H, s); 4.20–4.80 (4H+water, s); 3.71 (2H, s); 3.38 (2H, d); 3.12 (2H, d); 2.99–3.05 (4H, m); 1.99 (3H, s); 1.97 (3H, s); 1.81 (2H, quin); 1.68 (6H, q); 1.57 (6H, s).

EXAMPLE 5

5-[2-(2-Aminoethylamino)ethylamino]-2-chloro-N-(tricyclo[3.3.1.1$^{3,7}$]dec-1-ylmethyl)-benzamide, acetate

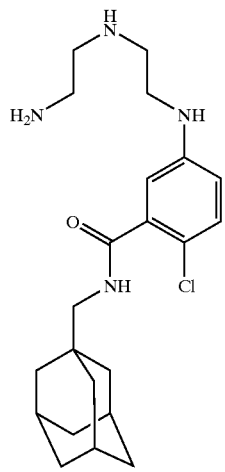

a) [2-[2-[4-chloro-3-(tricyclo[3.3.1.1$^{3,7}$]dec-1-ylmethylcarbamoyl)-phenylamino]-ethylamino]ethyl]-carbamic acid, 1,1-dimethylethyl ester Prepared according to the method of Example 4 using 2-chloro-5-(2-chloroethyl)amino-N-(tricyclo[3.3.1.1$^{3,7}$]dec-1-ylmethyl)-benzamide (WO 99/29661) (0.2 g) and (2-amino-ethyl)-carbamic acid tert butyl ester (0.25 g) to deliver the sub-title compound as a brown oil (0.25 g).

MS (APCI+ve) 405/407 (M+H−Boc)+ b) 5-[2-(2-Aminoethylamino)ethylamino]-2-chloro-N-(tricyclo[3.3.1.1$^{3,7}$]dec-1-ylmethyl)-benzamide, acetate 4M HCl in dioxane (2 ml) was added to a solution of [2-[2-[4-chloro-3-(tricyclo[3.3.1.1$^{3,7}$]dec-1-ylmethylcarbamoyl)-phenylamino]-ethylamino]ethyl]-carbamic acid, 1,1-dimethylethyl ester (0.25 g, Example 5a) in isopropanol (5 ml). After 15 h the reaction mixture was concentrated and the residue purified by RPHPLC (eluting with 15–95% MeCN in 0.1% AcONH$_4$ aqueous) to afford the title compound as solid (0.035).

MS (APCI+ve) 405/407 (M+H)+

$^1$H NMR (CDCl$_3$) δ7.12 (1H, d); 7.00 (1H, d); 6.61 (1H, dd); 6.50 (1H, t); 3.28 (2H, s); 3.10 (2H, d); 3.02 (2H, s); 2.95 (4H, s); 2.20–2.80 (5H+water, s); 1.99 (6H, q); 1.68 (6H, q); 1.57 (6H, s).

EXAMPLE 6

5-[2-(2-Acetylaminoethylamino)ethylamino]-2-chloro-N-(tricyclo[3.3.1.1$^{3,7}$]dec-1-ylmethyl)-benzamide, acetate

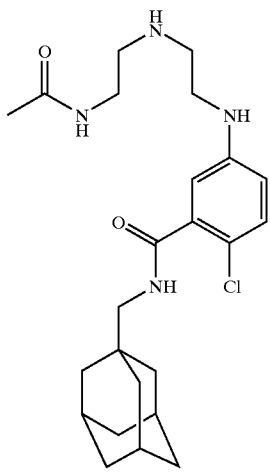

Prepared according to the method of Example 4 using 2-chloro-5-(2-chloroethylamino)-N-(tricyclo[3.3.1.1$^{3,7}$]dec-1-ylmethyl)-benzamide (WO 99/29661) (0.2 g) and N-(2-amino-ethyl)-acetamide (0.16 g) to deliver the title compound as a solid (0.03 g).

MS (APCI+ve) 447/449 (M+H)$^+$ $^1$H NMR (CDCl$_3$) δ7.15 (1H, d); 6.95 (1H, d); 6.68 (1H, s); 6.60 (1H, dd); 6.47 (1H, t); 3.41 (2H, q); 3.33 (2H, t); 3.15 (2H, d); 2.99 (2H, t); 2.87 (2H, t); 2.20–2.60 (3H+water, s); 1.99 (3H, s); 1.98 (3H, s); 1.95 (3H, s); 1.68 (6H, q); 1.58 (6H, s).

EXAMPLE 7

[2-[4-Chloro-3-(tricyclo[3.3.1.1$^{3,7}$]dec-1-ylmethyl) carbamoyl-phenylamino]-ethylamino]-propionic acid

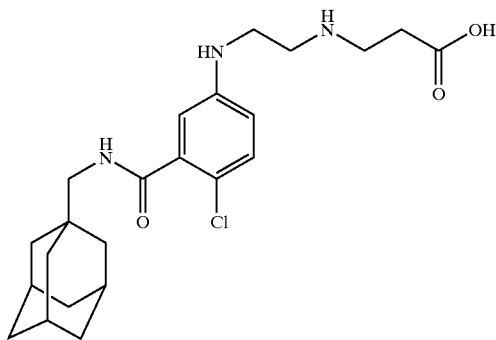

a) [2-[4-Chloro-3-(tricyclo[3.3.1.1$^{3,7}$]dec-1-ylmethyl) carbamoyl-phenylamino]-ethylamino]-propionic acid, 1,1-dimethylethyl ester Prepared according to the method of Example 4 using 2-chloro-5-(2-chloroethyl)amino-N-(tricyclo[3.3.1.1$^{3,7}$]dec-1-ylmethyl)-benzamide (WO 99/29661) (0.2 g) and β-alanine 1,1-dimethylethyl ester (0.29 g) to deliver the sub-title compound as an oil (0.20 g).

MS (APCI+ve) 490/492 (M+H)$^+$ b) [2-[4-Chloro-3-(tricyclo[3.3.1.1$^{3,7}$]dec-1-ylmethyl) carbamoyl-phenylamino]-ethylamino]-propionic acid To a solution of [2-[4-chloro-3-(tricyclo[3.3.1.1$^{3,7}$]dec-1-ylmethyl)carbamoyl-phenylamino]-ethylamino]-propionic acid, 1,1-dimethylethyl ester (0.20 g, Example 7a) in dichloromethane (5 ml), was added trifluoroacetic acid (2 ml). After 15 h the solution was concentrated and purified by RPHPLC (eluting with 15–95% MeCN in 0.1% AcONH$_4$ aqueous) to afford the title compound as a solid (0.010 g).

MS (APCI+ve) 434/436 (M+H)$^+$ $^1$H NMR (CDCl$_3$/d$_6$-DMSO/d$_1$-TFA/CD$_3$OD) δ7.18 (1H, d); 6.78 (1H, d); 6.68 (1H, dd); 3.50 (2H, t); 3.25 (2H, t); 3.22 (2H, t); 3.10 (2H, s); 2.78 (2H, t); 2.00 (3H, s); 1.69 (6H, q); 1.59 (6H, s).

EXAMPLE 8

2-Chloro-5-[2-(2-methylcarbamoylethylamino) ethylamino]-N-(tricyclo[3.3.1.1$^{3,7}$]dec-1-ylmethyl)-benzamide, acetate

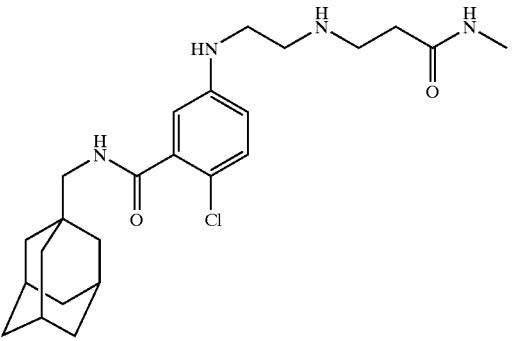

Prepared according to the method of Example 4 using 2-chloro-5-(2-chloroethylamino)-N-(tricyclo[3.3.1.1$^{3,7}$]dec-1-ylmethyl)-benzamide (WO 99/29661) (0.2 g) (0.2 g) and 3-amino-N-methylpropionamide (0.22 g) to give the title compound (0.08 g).

MS (APCI+ve) 447/449 (M+H)$^+$ $^1$H NMR (CDCl$_3$) δ7.13 (1H, d); 6.90 (1H, d); 6.59 (1H, dd); 6.20–6.40 (5H+water, m); 3.40 (2H, t); 3.14 (2H, d); 3.08–3.01 (4H, m); 2.73 (2H, d); 2.52 (2H, t); 2.00 (6H, s); 1.68 (6H, q); 1.58 (6H, s).

EXAMPLE 9

2-Chloro-5-[2-(2-dimethylcarbamoylethylamino) ethylamino]-N-(tricyclo[3.3.1.1$^{3,7}$]dec-1-ylmethyl)-benzamide, acetate

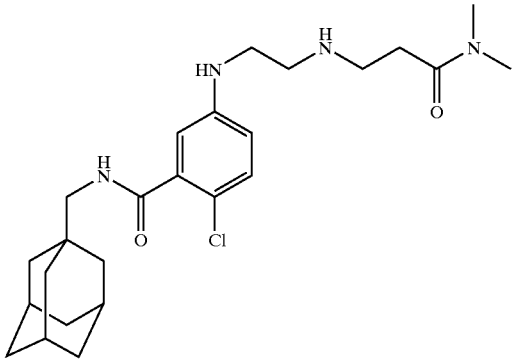

Prepared according to the method of Example 4 using 2-chloro-5-(2-chloroethylamino)-N-(tricyclo[3.3.1.1$^{3,7}$]dec-1-ylmethyl)-benzamide (WO 99/29661) (0.2 g) (0.2 g) and 3-amino-N,N-dimethylpropionamide (0.23 g) to deliver the title compound (0.005 g).

MS (APCI+ve) 461/463 (M+H)$^+$ $^1$H NMR (CDCl$_3$) δ7.14 (1H, d); 6.95 (1H, d); 6.63 (1H, dd); 6.37 (1H, t); 3.35 (2H, t); 3.16 (2H, d); 3.02–2.99 (7H, m); 2.94 (3H, s); 2.63 (2H, t); 2.60–2.20 (3H+water, s); 2.05 (3H, s); 2.00 (3H, s); 1.69 (6H, q); 1.58 (6H, s).

EXAMPLE 10

2-Chloro-5-[3-(3-hydroxypropylthio)propoxy]-N-(tricyclo[3.3.1.1$^{3,7}$]dec-1-ylmethyl)-benzamide

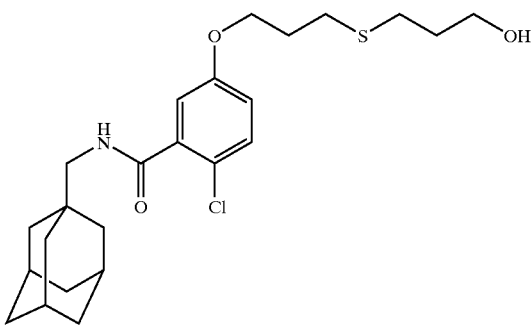

To a solution of 2-chloro-5-[3-chloropropoxy]-N-(tricyclo[3.3.1.1$^{3,7}$]dec-1-ylmethyl)-benzamide (0.06 g, Example 3a) and 1,8-diazabicyclo(5.4.0)undec-7-ene (0.07 ml) in 1-butanol (5 ml) was added sodium iodide (0.023 g) and 3-mecaptopropan-1-ol (0.04 ml). The reaction vessel was sealed and the mixture heated at 100° C. for 24 h. The reaction mixture was diluted with ethyl acetate and washed twice with 2M hydrochloric acid, twice with sodium hydrogencarbonate solution and once with brine. The organics were dried (MgSO$_4$) and concentrated under reduced pressure. The residue was purified by NPHPLC (eluting with 0–2% ethanol in dichloromethane) to leave the title compound as a white solid (0.05 g).

MS (APCI+ve) 452/454 (M+H)$^+$ $^1$H NMR (CDCl$_3$) δ7.29–7.26 (2H, m); 6.90 (1H, dd); 6.36 (1H, t); 4.09 (2H, t); 3.76 (2H, q); 3.17 (2H, d); 2.71 (2H, t); 2.65 (2H, t); 2.06 (2H, quin); 2.00 (3H, s); 1.85 (2H, quin); 1.69 (6H, q); 1.58 (6H, s).

EXAMPLE 11

5-[2-(2-Aminoethylthio)ethoxy]-2-chloro-N-(tricyclo[3.3.1.1$^{3,7}$]dec-1-ylmethyl)-benzamide, hydrochloride

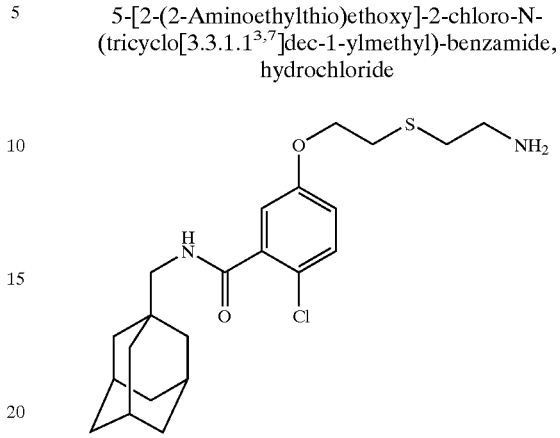

a) 2-Chloro-5-[2-chloroethoxy]-N-(tricyclo[3.3.1.1$^{3,7}$]dec-1-ylmethyl)-benzamide To a solution of 2-chloro-5-hydroxy-N-(tricyclo[3.3.1.1$^{3,7}$]dec-1-ylmethyl)-benzamide (WO 99/29661) (0.30 g), triphenylphosphine (0.25 g) and 2-chloroethanol (0.07 ml) in tetrahydrofuran (4 ml) was added diethyl azodicarboxylate (0.15 ml) and the reaction mixture stirred at room temperature for 18 h. Further triphenylphosphine (0.12 g) and diethyl azodicarboxylate (0.08 ml) were added and the reaction stirred for an additional 4 h. Silica was added and the reaction mixture concentrated under reduced pressure. The residue was purified by silica gel chromatography (eluting with 20% ethyl acetate in isohexanes) to deliver the sub-title compound as a lightly coloured oil (0.31 g).

$^1$H NMR (d$_6$-DMSO) δ8.30 (1H, t); 7.39 (1H, d); 7.03 (1H, dd); 6.96 (1H, d); 4.29 (2H, t); 4.04 (2H, t); 2.92 (2H, d); 1.93 (3H, s); 1.72–1.44 (12H, m).

b) [2-[3-[4-Chloro-3-(tricyclo[3.3.1.1$^{3,7}$]dec-1-ylmethylcarbamoyl)-phenoxy]-ethylthio]ethyl]-carbamic acid, 1,1-dimethylethyl ester To a solution of 2-chloro-5-[2-chloroethoxy]-N-(tricyclo[3.3.1.1$^{3,7}$]dec-1-ylmethyl)-benzamide (0.1 g, Example 11a) and 1,8-diazabicyclo(5.4.0)undec-7-ene (0.12 ml) in isopropanol (3 ml) was added sodium iodide (0.04 g) and (2-mercapto-ethyl)-carbamic acid tert butyl ester (0.14 ml). The reaction vessel was sealed and the mixture heated at 100° C. for 24 h. The reaction mixture was diluted with ethyl acetate and extracted twice with 2M hydrochloric acid, twice with sodium hydrogencarbonate solution and once with brine. The organics were dried (MgSO$_4$) and concentrated under reduced pressure. The residue was purified by NPH-PLC (eluting with 0–2% ethanol in dichloromethane) to afford the sub-title compound (0.32 g).

MS (APCI+ve) 523/525 (M+H)$^+$ c) 5-[2-(2-Aminoethylthio)ethoxy]-2-chloro-N-(tricyclo[3.3.1.1$^{3,7}$]dec-1-ylmethyl)-benzamide hydrochloride 4M HCl in dioxane (2 ml) was added to a solution of [2-[3-[4-chloro-3-(tricyclo[3.3.1.1$^{3,7}$]dec-1-ylmethylcarbamoyl)-phenoxy]-ethylthio]ethyl]-carbamic acid, 1,1-dimethylethyl ester (230 mg, Example 11b) in methanol (5 ml). After 15 h the solution was concentrated then purified by RPHPLC (eluting with 15–50% MeCN in 0.1% AcONH$_4$ aqueous) to afford the title compound as the acetate salt. The acetate salt was converted to the hydrochloride salt by stirring with 4M HCl in 1,4-dioxane. Concentration and trituration with diethyl ether gave the title compound as a solid (0.055 g).

MS (APCI+ve) 423/425 (M+H)$^+$ $^1$H NMR (d6-DMSO) δ8.30 (1H, t); 7.95 (3H, s); 7.39 (1H, d); 7.02 (1H, dd); 6.94 (1H, d); 4.19 (2H, t); 3.02–2.91 (6H, m); 2.85 (2H, t); 1.94 (3H, s); 1.63 (6H, q); 1.52 (6H, s).

EXAMPLE 12

2-Chloro-5-[2-(3-hydroxypropylamino)ethoxy]-N-(tricyclo[3.3.1.1$^{3,7}$]dec-1-ylmethyl)-benzamide, hydrochloride

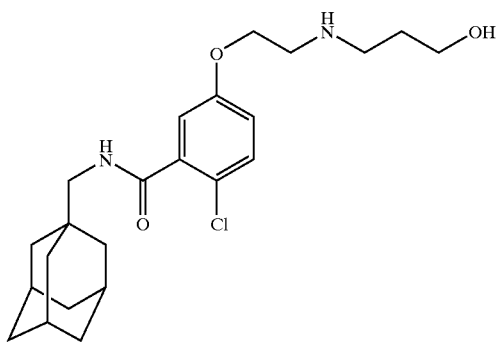

To a solution of 2-chloro-5-[2-chloroethoxy]-N-(tricyclo [3.3.1.1$^{3,7}$]dec-1-ylmethyl)-benzamide (Example 11a, 0.15 g) and N,N-diisopropylethylamine (0.50 ml) in 1-butanol (4 ml) was added sodium iodide (0.06 g) and 3-aminopropan-1-ol (0.09 ml). The reaction vessel was sealed and the mixture heated at 110° C. for 24 h. The reaction mixture was partitioned between ethyl acetate and sodium hydrogencarbonate solution, dried (MgSO$_4$) and concentrated under reduced pressure. The residue was purified by RPHPLC (eluting with 25–95% MeCN/0.1% AcONH$_4$ aqueous) to give 2-chloro-5-[2-[(3-hydroxypropyl)amino]ethoxy]-N-(tricyclo[3.3.1.1$^{3,7}$]dec-1-ylmethyl)-benzamide as the acetate salt. This was converted to the hydrochloride salt by stirring with 4M HCl in dioxane and concentration under reduced pressure. Recrystalisation from isohexane/isopropanol gave the title compound as a white solid (0.1 g).

MS (APCI+ve) 421/423 (M+H)$^+$ $^1$H NMR (d6-DMSO) δ8.08 (2H, s); 8.32 (1H, t); 7.43 (1H, d); 7.06 (1H, dd); 6.98 (1H, d); 4.79 (1H, t); 4.27 (2H, t); 3.49 (2H, q); 3.40 (2H, s); 3.05 (2H, s); 2.93 (2H, d); 1.94 (3H, s); 1.79 (2H, quin); 1.58 (6H, q); 1.52 (6H, s).

EXAMPLE 13

2-Chloro-5-[3-(3-hydroxypropylsulfonyl)propoxy]-N-(tricyclo[3.3.1.1$^{3,7}$]dec-1-ylmethyl)-benzamide

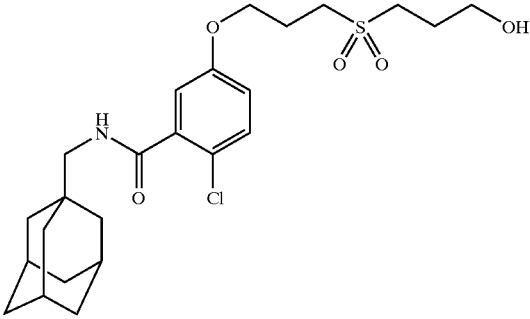

3-Chloroperoxybenzoic acid (0.14 g, 70%) was added to a solution of 2-chloro-5-[3-(3-hydroxypropylthio)propoxy]-N-(tricyclo[3.3.1.1$^{3,7}$]dec-1-ylmethyl)-benzamide (Example 10, 0.1 g) in dichloromethane (10 ml). After 1 hour calcium hydroxide (0.1 g) was added and stirring continued for a further 30 min. The reaction mixture was dried (MgSO$_4$), filtered through celite and concentrated. The residue was triturated with ethanol to leave the title compound as a white solid (0.030 g).

MS (APCI+ve) 484/486 (M+H)$^+$ $^1$H NMR (d6-DMSO) δ8.29 (1H, t); 7.38 (1H, d); 7.00 (1H, dd); 6.93 (1H, d); 4.68 (1H, t); 4.11 (2H, t); 3.49 (2H, q); 3.25 (2H, t); 3.14 (2H, t); 2.92 (2H, d); 2.12 (2H, quin); 1.94 (3H, s); 1.85 (2H, quin); 1.63 (6H, q); 1.52 (6H, s).

EXAMPLE 14

(±)-2-Chloro-5-13-(3-hydroxypropylsulfinyl) propoxy]-N-(tricyclo[3.3.1.1$^{3,7}$]dec-1-ylmethyl)-benzamide

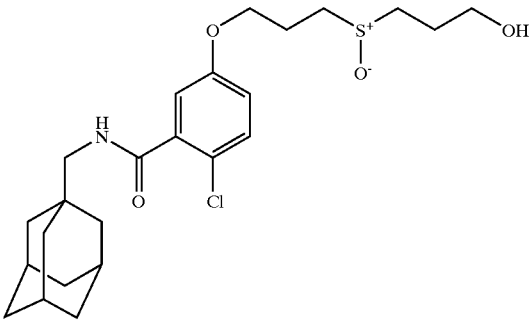

3-Chloroperoxybenzoic acid (0.065 g, 70%) was added to a solution of 2-chloro-5-[3-(3-hydroxypropylthio)propoxy]-N-(tricyclo[3.3.1.1$^{3,7}$]dec-1-ylmethyl)-benzamide (Example 10, 0.11 g) in dichloromethane (10 ml). After 15 h the crude reaction mixture was purified by NPHPLC (eluting 0–10% ethanol in dichloromethane) to leave the title compound as a white solid (0.055 g).

MS (APCI+ve) 468/470 (M+H)$^+$ $^1$H NMR (d6-DMSO) δ8.29 (1H, t); 7.37 (1H, d); 7.00 (1H, dd); 6.93 (1H, d); 4.63 (1H, t); 4.12 (2H, t); 3.50 (2H, q); 3.00–2.64 (6H, m); 2.09 (2H, quin); 1.94 (3H, s); 1.80 (2H, quin); 1.62 (6H, q); 1.52 (6H, s).

EXAMPLE 15

2-Chloro-5-[2-(3-hydroxypropylthio)ethoxy]-N-(tricyclo[3.3.1.1^{3,7}]dec-1-ylmethyl)-benzamide

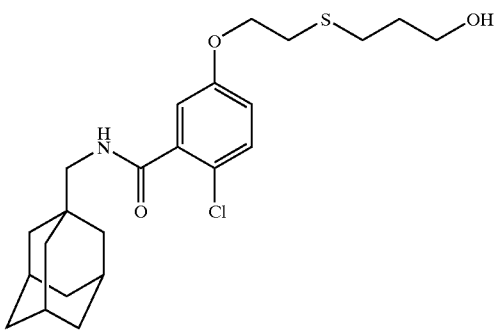

Prepared according to the method of Example 10 using 2-chloro-5-(2-chloroethoxy)-N-(tricyclo[3.3.1.1^{3,7}]dec-1-ylmethyl)-benzamide (Example 11a, 0.34 g) and 3-mercaptopropan-1-ol (0.25 ml) to give the title compound (0.4 g).

MS (APCI+ve) 438/440 (M+H)+

$^1$H NMR (d6-DMSO) δ8.28 (1H, t); 7.37 (1H, d); 7.00 (1H, dd); 6.92 (1H, d); 4.47 (1H, t); 4.15 (2H, t); 3.45 (2H, q); 2.92 (2H, d); 2.86 (2H, t); 2.63 (2H, t); 1.94 (3H, s); 1.72–1.57 (8H, m); 1.51 (6H, s).

EXAMPLE 16

(S)-2-Chloro-5-[2-(2-hydroxypropylamino)ethoxy]-N-(tricyclo[3.3.1.1^{3,7}]dec-1-ylmethyl)-benzamide, hydrochloride

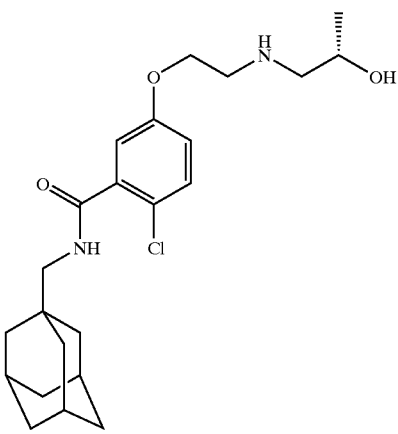

Chiral

Prepared according to the method of Example 4 using 2-chloro-5-(2-chloroethoxy)-N-(tricyclo[3.3.1.1^{3,7}]dec-1-ylmethyl)-benzamide (0.17 g, Example 11a) and (S)-1-amino-2-propanol (0.11 ml). The reaction mixture was partitioned between ethyl acetate and sodium hydrogencarbonate solution, dried (MgSO$_4$) and concentrated under reduced pressure. The residue was purified by RPHPLC (eluting with 25–95% MeCN in 0.1% AcONH$_4$ aqueous) to give the title compound as the acetate salt. This was converted to the hydrochloride salt by stirring with 4M HCl in dioxane and concentration under reduced pressure. Recrystalisation from isohexane/isopropanol gave the title compound as a solid (0.05 g).

MS (APCI+ve) 421/423 (M+H)+

$^1$H NMR (d6-DMSO) δ8.80 (2H, d); 8.32 (1H, t); 7.42 (1H, d); 7.05 (1H, dd); 6.98 (1H, d); 5.36 (1H, d); 4.29 (2H, t); 4.05–3.95 (1H, m); 3.35 (2H, s); 3.10–3.00 (1H, m); 2.93 (2H, d); 2.85 (1H, m); 1.94 (3H, s); 1.63 (6H, q); 1.52 (6H, s); 1.12 (3H, d).

EXAMPLE 17

(R)-2-Chloro-5-[2-(2-hydroxypropylamino)ethoxy]-N-(tricyclo[3.3.1.1^{3,7}]dec-1-ylmethyl)-benzamide, hydrochloride

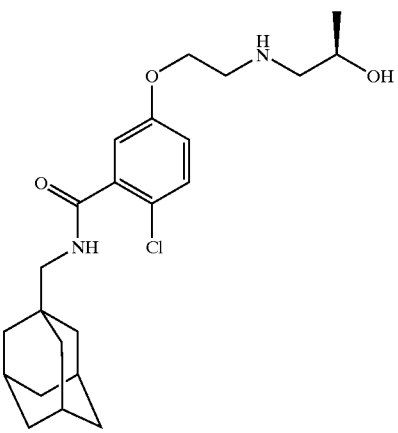

Chiral

Prepared according to the method of Example 4 using 2-chloro-5-(2-chloroethoxy)-N-(tricyclo[3.3.1.1^{3,7}]dec-1-ylmethyl)-benzamide (Example 11a, 0.17 g) and (R)-1-amino-2-propanol (0.11 ml). The reaction mixture was partitioned between ethyl acetate and sodium hydrogencarbonate solution, dried (MgSO$_4$) and concentrated under reduced pressure. The residue was purified by RPHPLC (eluting with 25–95% MeCN in 0.1% AcONH$_4$ aqueous) to give the title compound as the acetate salt. This was converted to the hydrochloride salt by stirring with 4M HCl in dioxane and concentration under reduced pressure. Trituration with diethyl ether gave the title compound as a solid (0.055 g).

MS (APCI+ve) 421/423 (M+H)+

$^1$H NMR (d6-DMSO) δ8.8 (2H, m); 8.32 (1H, t); 7.42 (1H, d); 7.05 (1H, dd); 6.98 (1H, d); 5.36 (1H, d); 4.29 (2H, t); 4.05–3.95 (1H, m); 3.35 (2H, s); 3.10–3.00 (1H, m); 2.93 (2H, d); 2.90–2.80 (1H, m); 1.94 (3H, s); 1.63 (6H, q); 1.52 (6H, s); 1.12 (3H, d).

EXAMPLE 18

(d)-2-Chloro-5-[2-(2-hydroxy-1-methylethylamino)ethoxy]-N-(tricyclo[3.3.1.1$^{3,7}$]dec-1-ylmethyl)-benzamide, hydrochloride

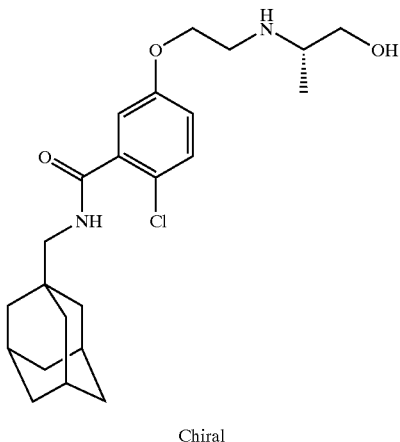

Chiral

Prepared according to the method of Example 4 using 2-chloro-5-(2-chloroethoxy)-N-(tricyclo[3.3.1.1$^{3,7}$]dec-1-ylmethyl)-benzamide (Example 11a, 0.17 g) and (S)-2-amino-1-propanol (0.11 ml). The reaction mixture was partitioned between ethyl acetate and sodium hydrogencarbonate solution, dried (MgSO$_4$) and concentrated under reduced pressure. The residue was purified by RPHPLC (eluting with 25–95% MeCN in 0.1% AcONH$_4$ aqueous) to give the title compound as the acetate salt. This was converted to the hydrochloride salt by stirring with 4M HCl in dioxane and concentration under reduced pressure. Trituration with diethyl ether gave the title compound as a solid (0.07 g).

MS (APCI+ve) 421/423 (M+H)$^+$ $^1$H NMR (d6-DMSO) δ8.75 (2H, d); 8.32 (1H, t); 7.42 (1H, d); 7.05 (1H, dd); 6.99 (1H, d); 5.40 (1H, t); 4.29 (2H, t); 3.69–3.63 (1H, m); 3.56–3.50 (1H, m); 3.40–3.30 (3H+water, s); 2.93 (2H, d); 1.94 (3H, s); 1.63 (6H, q); 1.52 (6H, s); 1.22 (3H, d).

EXAMPLE 19

(R)-2-Chloro-5-[2-(2-hydroxy-1-methylethylamino)ethoxy]-N-(tricyclo[3.3.1.1$^{3,7}$]dec-1-ylmethyl)-benzamide, hydrochloride

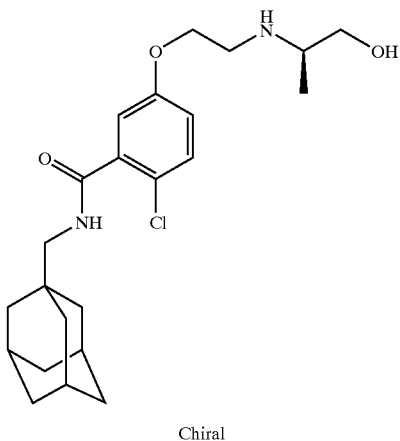

Chiral

Prepared according to the method of Example 4 using 2-chloro-5-(2-chloroethoxy)-N-(tricyclo[3.3.1.1$^{3,7}$]dec-1-ylmethyl)-benzamide (Example 11a, 0.17 g) and (R)-2-amino-1-propanol (0.11 ml). The reaction mixture was partitioned between ethyl acetate and sodium hydrogencarbonate solution, dried (MgSO$_4$) and concentrated under reduced pressure. The residue was purified by RPHPLC (eluting with 25–95% MeCN in 0.1% AcONH$_4$ aqueous) to give the title compound as the acetate salt. This was converted to the hydrochloride salt by stirring with 4M HCl in dioxane and concentrated under reduced pressure. Trituration with diethyl ether gave the title compound as a solid (0.05 g).

MS (APCI+ve) 421/423 (M+H)$^+$ $^1$H NMR (d6-DMSO) δ8.75 (2H, d); 8.32 (1H, t); 7.42 (1H, d); 7.05 (1H, dd); 6.99 (1H, d); 5.40 (1H, t); 4.29 (2H, t); 3.69–3.63 (1H, m); 3.56–3.50 (1H, m); 3.40–3.30 (3+water, s); 2.93 (2H, d); 1.94 (3H, s); 1.63 (6H, q); 1.52 (6H, s); 1.22 (3H, d).

EXAMPLE 20

(±)-2-Chloro-5-[2-(3-hydroxypropylsulfinyl)ethoxy]-N-(tricyclo[3.3.1.1$^{3,7}$]dec-1-ylmethyl)-benzamide

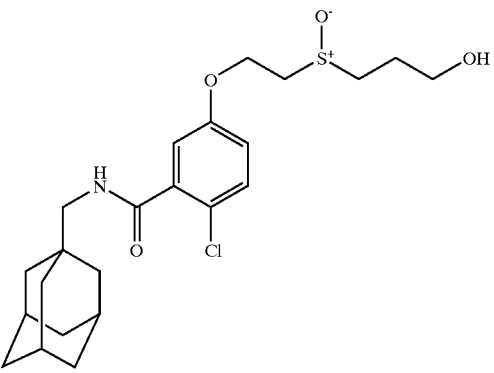

Prepared according to the method of Example 14 using 2-chloro-5-[2-(3-hydroxypropylthio)ethoxy]-N-(tricyclo[3.3.1.1$^{3,7}$]dec-1-ylmethyl)-benzamide (Example 15, 0.12 g) and 3-chloroperoxybenzoic acid (0.07 g, 70%) to give the title compound (0.07 g).

MS (APCI+ve) 454/456 (M+H)$^+$ $^1$H NMR (d6-DMSO) δ8.31 (1H, t); 7.39 (1H, d); 7.05 (1H, dd); 6.97 (1H, d); 4.64 (1H, t); 4.30–4.50 (2H, m); 3.55 (2H, q); 3.30–3.22 (1H, m); 3.07–3.01 (1H, m); 2.93–2.83 (3H, m); 2.81–2.74 (1H, m); 1.94 (3H, s); 1.80 (2H, quin); 1.66 (6H, q); 1.52 (6H, s).

EXAMPLE 21

2-Chloro-5-[2-(3-hydroxypropylsulfonyl)ethoxy]-N-(tricyclo[3.3.1.1$^{3,7}$]dec-1-ylmethyl)-benzamide

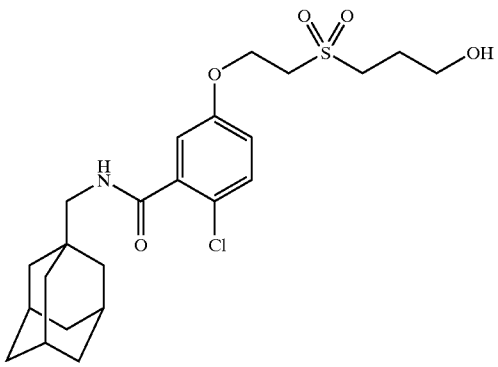

Prepared according to the method of Example 13 using 2-chloro-5-[2-(3-hydroxypropylthio)ethoxy]-N-(tricyclo[3.3.1.1$^{3,7}$]dec-1-ylmethyl)-benzamide (Example 15, 0.12 g) and 3-chloroperoxybenzoic acid (0.14 g, 70%). Purification by NPHPLC (eluting 0–5% EtOH in dichloromethane) gave the title compound (0.07 g).

MS (APCI+ve) 470/472 (M+H)$^+$ $^1$H NMR (d6-DMSO) δ8.31 (1H, t); 7.40 (1H, d); 7.05 (1H, dd); 6.98 (1H, d); 4.70 (1H, t); 4.38 (2H, t); 3.62 (2H, t); 3.50 (2H, q); 3.20 (2H, t); 2.92 (2H, d); 1.94 (3H, s); 185 (2H, quin); 1.66 (6H, q); 1.52 (6H, s).

EXAMPLE 22

(±)-5-[2-(2-Aminoethylsulfinyl)ethoxy]-2-chloro-N-(tricyclo[3.3.1.1$^{3,7}$]dec-1-ylmethyl)-benzamide, hydrochloride

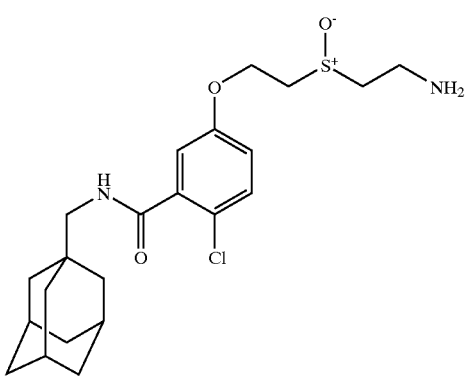

a) [2-[3-[4-Chloro-3-(tricyclo[3.3.1.1$^{3,7}$]dec-1-ylmethylcarbamoyl)-phenoxy]-ethylsulfinyl]ethyl]-carbamic acid, 1,1-dimethylethyl ester 3-Chloroperoxybenzoic acid (0.1 g, 70%) was added to a solution of [2-[3-[4-chloro-3-(tricyclo[3.3.1.1$^{3,7}$]dec-1-ylmethylcarbamoyl)-phenoxy]-ethylthiolethyl]-carbamic acid, 1,1-dimethylethyl ester (Example 11b, 0.2 g) in dichloromethane (10 ml). After 2 h calcium hydroxide (0.3 g) was added and stirring continued for a further 30 minutes. The reaction mixture was dried (MgSO$_4$), filtered through celite and concentrated. Purification by NPHPLC (eluting with 0–10% ethanol in dichloromethane) gave the sub-title compound (0.14 g).

MS (APCI+ve) 439/441 (M+H–Boc)$^+$ b) (±)-5-[2-(2-Aminoethylsulfinyl)ethoxy]-2-chloro-N-(tricyclo[3.3.1.1$^{3,7}$]dec-1-ylmethyl)-benzamide, hydrochloride 4M hydrochloric acid in dioxane (2 ml) was added to a solution of [2-[3-[4-chloro-3-(tricyclo[3.3.1.1$^{3,7}$]dec-1-ylmethylcarbamoyl)-phenoxy]-ethylsulfinyl]ethyl]-carbamic acid, 1,1-dimethylethyl ester (0.14 g) in methanol (10 ml). After 15 h the reaction mixture was concentrated and the residue recrystallised from isohexane/isopropanol, to afford the title product (0.05 g).

MS (APCI+ve) 439/441 (M+H)$^+$ $^1$H NMR (d6-DMSO) δ8.32 (1H, t); 8.06 (3H, s); 7.40 (1H, d); 7.07 (1H, dd); 6.99 (1H, d); 4.45–4.30 (2H, m); 3.45–3.05 (6H, m); 2.92 (2H, d); 1.94 (3H, s); 1.85 (2H, quin); 1.63 (6H, q); 1.52 (6H, s).

EXAMPLE 23

5-[2-(2-Aminoethylsulfonyl)ethoxy]-2-chloro-N-(tricyclo[3.3.1.1$^{3,7}$]dec-1-ylmethyl)-benzamide, hydrochloride

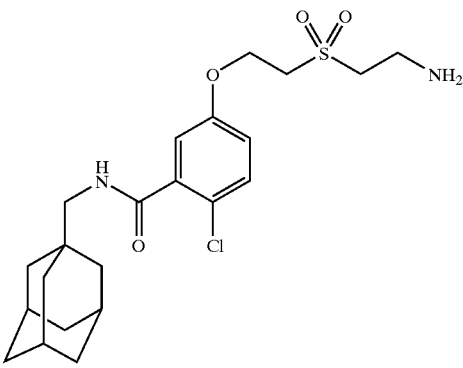

a) [2-[3-[4-Chloro-3-(tricyclo[3.3.1.1$^{3,7}$]dec-1-ylmethylcarbamoyl)-phenoxy]-ethylsulfonyl]ethyl]-carbamic acid, 1,1-dimethylethyl ester 3-Chloroperoxybenzoic acid (0.3 g, 70%) was added to a solution of [2-[3-[4-chloro-3-(tricyclo[3.3.1.1$^{3,7}$]dec-1-ylmethylcarbamoyl)-phenoxy]-ethylthio]ethyl]-carbamic acid, 1,1-dimethylethyl ester (Example 11b, 0.2 g) in dichloromethane (10 ml). After 2 h calcium hydroxide (0.3 g) was added and stirring continued for a further 30 min. The reaction mixture was dried (MgSO$_4$), filtered through celite and concentrated. Purification by NPHPLC (eluting with 0–10% ethanol in dichloromethane) afforded the sub-title compound (0.12 g).

MS (APCI+ve) 455/457 (M+H–BOC)$^+$ b) 5-[2-(2-Aminoethylsulfonyl)ethoxy]-2-chloro-N-(tricyclo[(3.3.1.1$^{3,7}$]dec-1-ylmethyl)-benzamide, hydrochloride 4M hydrochloric acid in dioxane (2 ml) was added to a solution of [2-[3-[4-chloro-3-(tricyclo[3.3.1.1$^{3,7}$]dec-1-ylmethylcarbamoyl)-phenoxy]-ethylsulfonyl]ethyl]-carbamic acid, 1,1-dimethylethyl ester (Example 23a, 0.14 g) in methanol (10 ml). After 15 h the reaction mixture was concentrated and the residue recrystallised from isohexane/isopropanol, to afford the title product (0.05 g).

MS (APCI+ve) 455/457 (M+H)$^+$ $^1$H NMR (d6-DMSO) δ8.32 (1H, t); 8.10 (3H, s); 7.42 (1H, d); 7.10 (1H, dd); 7.04 (1H, d); 4.40 (2H, t); 3.80 (2H, t); 3.55 (2H, t); 3.25 (2H, t); 2.95 (2H, d); 1.94 (3H, s); 1.63 (6H, q); 1.52 (6H, s).

EXAMPLE 24

5-[3-(2-Aminoethylthio)propoxy]-2-chloro-N-(tricyclo[3.3.1.1³,⁷]dec-1-ylmethyl)-benzamide, hydrochloride

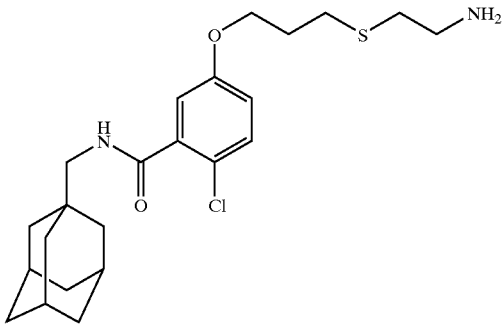

a) [2-[3-[4-Chloro-3-(tricyclo[3.3.1.1³,⁷]dec-1-ylmethylcarbamoyl)-phenoxy]-propylthio]ethyl]-carbamic acid, 1,1-dimethylethyl ester Prepared according to the method of Example 11b from 2-chloro-5-(3-chloropropoxy)-N-(tricyclo[3.3.1.1³,⁷]dec-1-ylmethyl)-benzamide (Example 3a, 0.47 g), to afford the sub-title compound (1.0 g).

MS (APCI+ve) 537/539 (M+H)⁺ b) 5-[3-(2-Aminoethylthio)propoxy]-2-chloro-N-(tricyclo[3.3.1.1³,⁷]dec-1-ylmethyl)-benzamide, hydrochloride Prepared according to the method of Example 11c from [2-[3-[4-chloro-3-(tricyclo[3.3.1.1³,⁷]dec-1-ylmethylcarbamoyl)-phenoxy]-propylthio]ethyl]-carbamic acid, 1,1-dimethylethyl ester (Example 24a, 0.34 g), to afford the title compound (0.065 g).

MS (APCI+ve) 437/439 (M+H)⁺

$^1$H NMR (d6-DMSO) δ8.29 (1H, t); 7.94 (3H, s); 7.37 (1H, d); 7.00 (1H, dd); 6.92 (1H, d); 4.07 (2H, t); 2.98 (2H, t); 2.92 (2H, d); 2.71 (2H, t); 2.66 (2H, t); 2.02–1.95 (5H, m); 1.63 (6H, q); 1.52 (6H, s).

EXAMPLE 25

(±)-5-[3-(2-Aminoethylsulfinyl)propoxy]-2-chloro-N-(tricyclo[3.3.1.1³,⁷]dec-1-ylmethyl)-benzamide, hydrochloride

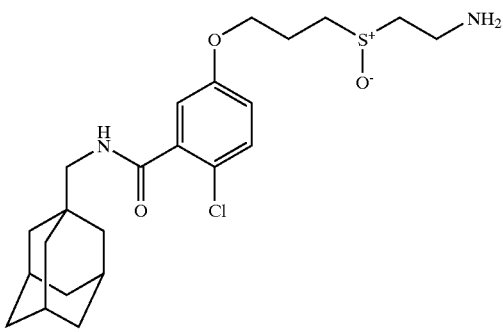

Prepared according to the method of Example 22 from [2-[3-[4-chloro-3-(tricyclo[3.3.1.1³,⁷]dec-1-ylmethylcarbamoyl)-phenoxy]-propylthio]ethyl]-carbamic acid, 1,1-dimethylethyl ester (Example 24a, 0.3 g), to give the title compound (0.16 g).

MS (APCI+ve) 453/455 (M+H)⁺

$^1$H NMR (d6-DMSO) δ8.30 (1H, t); 8.05 (3H, s); 7.38 (1H, d); 7.01 (1H, dd); 6.93 (1H, d); 4.13 (2H, t); 3.30–2.87 (8H, m); 2.10 (2H, quin); 1.94 (3H, s); 1.63 (6H, q); 1.52 (6H, s).

EXAMPLE 26

5-[3-(2-Aminoethylsulfonyl)propoxy]-2-chloro-N-(tricyclo[3.3.1.1³,⁷]dec-1-ylmethyl)-benzamide, hydrochloride

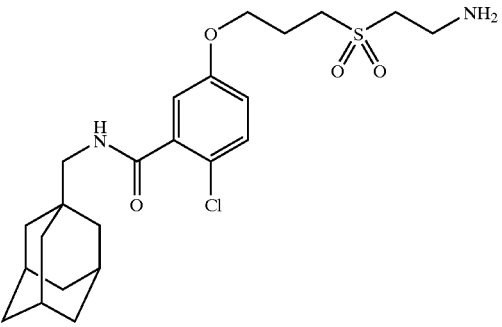

Prepared according to the method of Example 23 using [2-[3-[4-chloro-3-(tricyclo[3.3.1.1³,⁷]dec-1-ylmethylcarbamoyl)-phenoxy]-propylthio]ethyl]-carbamic acid, 1,1-dimethylethyl ester (Example 24a, 0.2 g), to give the title compound (0.07 g).

MS (APCI+ve) 469/471 (M+H)⁺

$^1$H NMR (d6-DMSO) δ8.30 (1H, t); 8.12 (3H, s); 7.39 (1H, d); 7.02 (1H, dd); 6.94 (1H, d); 4.15 (2H, t); 3.60–3.20 (6H+water, m); 2.92 (2H, d); 2.12 (2H, quin); 1.94 (3H, s); 1.63 (6H, q); 1.53 (6H, s).

EXAMPLE 27

2-Chloro-5-[[2-[(3-hydroxy-3-methylbutyl)amino]ethyl]amino]-N-(tricyclo[3.3.1.1³,⁷]dec-1-ylmethyl)-benzamide

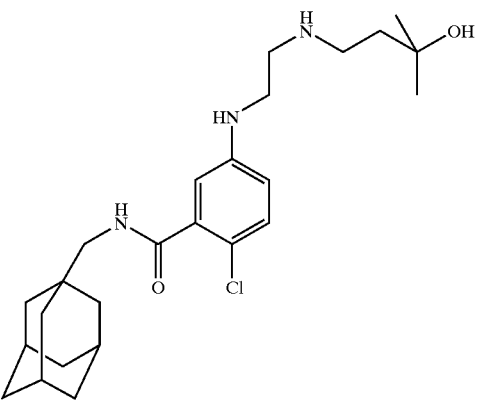

Prepared according to the method described in Example 1

MS (APCI+ve) 448/450 (M+H)⁺

$^1$H NMR (d6-DMSO) δ8.15 (1H, t); 7.10 (1H, d); 6.60–6.50 (2H, m); 5.86 (1H, t); 3.06 (2H, q); 2.89 (2H, d); 2.73–2.60 (4H, m); 1.93 (3H, s); 1.63 (6H, q); 1.52 (6H, q); 1.08 (6H, s).

EXAMPLE 28

2-Chloro-5-[2-[2-[(2-hydroxyethyl)amino]ethoxy]ethoxy]-N-(tricyclo[3.3.1.1³,⁷]dec-1-ylmethyl)-benzamide, hydrochloride

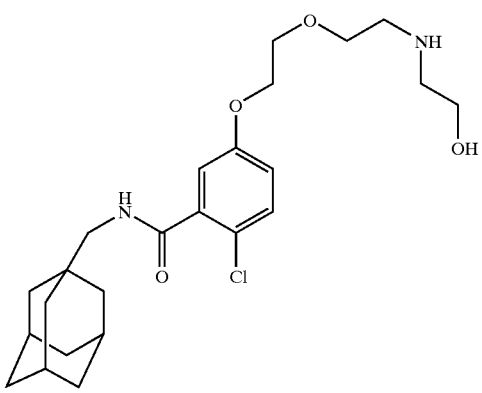

a) 2-Chloro-5-[2-[2-chloroethoxy]ethoxy]-N-(tricyclo[3.3.1.1³,⁷]dec-1-ylmethyl)-benzamide, Prepared according to the method of Example 11 a from 2-chloro-5-hydroxy-N-(tricyclo[3.3.1.1³,⁷]dec-1-ylmethyl)-benzamide (WO99/29661, 1.0 g), 2-(2-chloroethoxy)ethanol (0.5 ml), triphenylphosphine (1.0 g) and diethylazadicarboxylate (0.7 ml). Chromatography eluting with isohexane/ethyl acetate 4:1 to 7:3 gave the sub-title product as a solid (1.2 g).

MS (APCI+ve) 426/428/430 (M+H)⁺

¹H NMR (CDCl3) δ7.30–7.26 (2H, m); 6.93 (1H, dd); 6.33 (1H, t); 4.20 (2H, t); 3.88 (2H, t); 3.82 (2H, t); 3.65 (2H, t); 3.17 (2H, d); 2.00 (3H, s); 1.68 (6H, q); 1.58 (6H, s).

b) 2-Chloro-5-[2-[2-[(2-hydroxyethyl)amino]ethoxy]ethoxy]-N-(tricyclo[3.3.1.1³,⁷]dec-1-ylmethyl)-benzamide, hydrochloride 2-Hydroxyethylamine (0.15 ml) was added to a mixture of 2-chloro-5-[2-[2-chloroethoxy]ethoxy]-N-(tricyclo[3.3.1.1³,⁷]dec-1-ylmethyl)-benzamide (0.1 g, Example 28a), potassium iodide (0.005 g) and triethylamine (0.5 ml) in n-butanol (4 ml). The mixture was heated in a sealed tube at 100° C. for 24 h. After cooling, the reaction mixture was partitioned between ethyl acetate and water. The organics were separated and washed with water, then with saturated sodium hydrogencarbonate solution followed by brine. The combined organic extracts were dried over magnesium sulfate, filtered and evaporated. Purification by RP-HPLC eluting with a gradient of methanol/0.1% aqueous trifluoroacetic acid. Concentration gave the product as the trifluoroacetate salt, which was converted to the hydrochloride by treatment with 4M HCl in 1,4-dioxane to give the title product (0.030 g).

MS (APCI+ve) 451/453 (M+H)⁺

¹H NMR (d6-DMSO) δ8.62 (2H, brs); 8.29 (1H, t); 7.37 (1H, d); 7.01 (1H, dd); 6.93 (1H, d); 4.16 (2H, t); 3.85–3.70 (4H, m); 3.65 (2H, t); 3.17 (2H, quin); 3.02 (2H, quin); 2.92 (2H, d); 1.94 (3H, s); 1.63 (6H, q); 1.52 (6H, s).

EXAMPLE 29

2-Chloro-5-[[2-[[2-(methylthio)ethyl]amino]ethyl]amino]-N-(tricyclo[3.3.1.1³,⁷]dec-1-ylmethyl)-benzamide

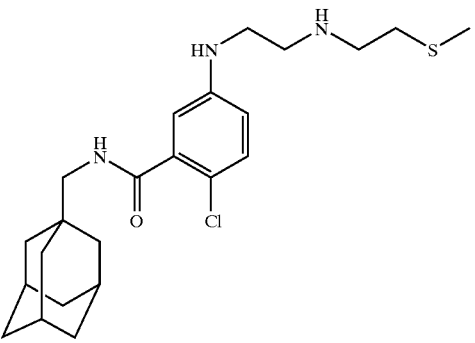

a) 2-Chloro-5-nitro-N-(tricyclo[3.3.1.1³,⁷]dec-1-ylmethyl)-benzamide

To a solution of 2-chloro-5-nitrobenzoic acid (1.22 g) in N,N-dimethylformamide (1.5 ml) was added 1,1-carbonyldiimidazole (1.0 g). The resulting reaction mixture was stirred for 2.5 h and then 1-adamantanemethylanine (1.0 g) was added. After 14 h the reaction mixture was partitioned between ethyl acetate and water and the organic layer was separated, washed with water and brine and then dried over sodium sulphate (Na₂SO₄). The organic layer was concentrated under reduced pressure to give a residue which was purified by silica gel chromatography (eluting with 3–10% methanol in dichloromethane) to yield the sub-title compound as a yellow solid (1.7 g).

MS (APCI+ve) 348/350 (M+H)⁺

¹H NMR (CDCl₃) δ8.53 (1H, d), 8.2 (1H, dd), 7.6 (1H, d), 6.2 (1H, bs), 3.2 (2H, d), 2.0 (3H, bs), 1.8 (12H, m)

b) 5-Amino-2-chloro-N-(tricyclo[3.3.1.1³,⁷]dec-1-ylmethyl)-benzamide

A solution of 2-chloro-5-nitro-N-(tricyclo[3.3.1.1³,⁷]dec-1-ylmethyl)-benzamide (Example 29a, 0.50 g) and ammonium chloride (0.5 g) were dissolved in 50% aqueous ethanol. Iron powder (0.5 g) was added and the mixture stirred at reflux temperature for 3 h before being cooled and the solids removed by filtration. The mother liquors were treated with 10% sodium hydroxide solution and the product extracted into ethyl acetate. The organic solution was washed with brine, dried over sodium sulphate (Na₂SO₄) and concentrated to give a residue which was purified by silica gel chromatography to give the sub-title compound as a white solid (0.4 g).

MS (APCI+ve) 319/321 (M+H)⁺

¹H NMR (d6-DMSO) δ8.14 (1H, t); 7.03 (1H, dd); 6.56 (2H, m); 5.36 (2H, s); 2.89 (2H, d); 1.95 (3H, s); 1.7 (12H, m)

c) 2-Chloro-5-[(2-chloroethyl)amino]-N-(tricyclo[3.3.1.1³,⁷]dec-1-ylmethyl)-benzamide 5-Amino-2-chloro-N-(tricyclo[3.3.1.1³,⁷]dec-1-ylmethyl)-benzamide (7 g, Example 29b) and chloroacetaldehyde (50% solution in water, 6.6 ml) were stirred in methanol (120 ml) under nitrogen for 10 min. A mixture of 6M hydrochloric acid (1.8 ml) and methanol (1.8 ml) was added, followed by sodium cyanoborohydride (1.48 g). The mixture was stirred for 2.5 h. The methanol was then removed under reduced pressure and the residue partitioned between saturated aqueous sodium hydrogencarbonate and dichloromethane The aqueous layer was extracted twice more with dichloromethane and the combined extracts were dried over magnesium sulfate, filtered and concentrated under reduced pressure to afford the sub-title compound (8.2 g).

MS (APCI+ve) 381/383/385 (M+H)+

$^1$H NMR (CDCl$_3$) δ7.18 (1H, d); 7.02–6.99 (1H, m); 6.64–6.61 (1H, m); 6.37 (1H, br s); 4.19 (1H, br t); 3.72–3.69 (2H, m); 3.53–3.49 (2H, m); 3.17 (2H, d); 2.01 (3H, br s); 1.69 (6H, m); 1.59 (6H, br s).

d) 2-Chloro-5-[[2-[[2-(methylthio)ethyl]amino]ethyl]amino]-N-(tricyclo[3.3.1.1$^{3,7}$]dec-1-ylmethyl)-benzamide 2-Chloro-5-[(2-chloroethyl)amino]-N-(tricyclo[3.3.1.1$^{3,7}$]dec-1-ylmethyl)-benzamide (0.200 g, Example 29c), 2-(methylthio)ethylamine (0.478 g), triethylamine (0.7 ml) and tetrahydrofuran (4 ml) were heated together in a sealed tube at 80° C. for 24 h. The mixture was cooled, poured into saturated aqueous sodium hydrogencarbonate solution and extracted into ethyl acetate. The combined extracts were dried over magnesium sulfate, filtered and concentrated under reduced pressure. The crude material was purified on silica gel (eluant 19:1/dichloromethane:methanol) to afford the title compound as a gum (0.129 g).

MS (APCI+ve) 436/438 (M+H)+

$^1$H NMR (CDCl$_3$) δ7.15 (1H, d); 6.97 (1H, d); 6.60 (1H, dd); 6.33 (1H, br t); 4.41 (1H, br t); 3.21–3.16 (4H, m); 2.91–2.82 (4H, m); 2.66 (2H, t); 2.17 (3H, s); 2.00 (3H, br s); 1.69 (6H, m); 1.58 (6H, br s).

EXAMPLE 30

2-Chloro-5-[[2-[[2-(methylsulfinyl)ethyl]amino]ethyl]amino]-N-(tricyclo[3.3.1.1$^{3,7}$]dec-1-ylmethyl)-benzamide, acetic acid salt

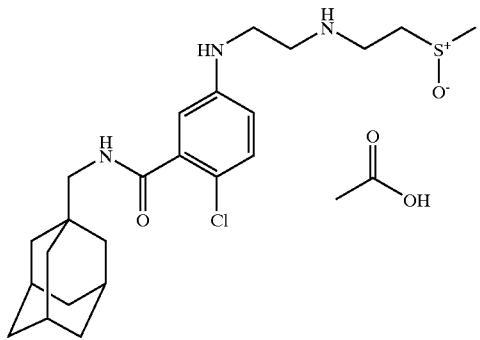

a) [2-[[4-Chloro-3-[[(tricyclo[3.3.1.1$^{3,7}$]dec-1-ylmethyl)amino]carbonyl]-phenyl]amino]ethyl][2-(methylthio)ethyl]-carbamic acid, 1,1-dimethylethyl ester 2-Chloro-5-[[2-[[2-(methylthio)ethyl]amino]ethyl]amino]-N-(tricyclo[3.3.1.1$^{3,7}$]dec-1-ylmethyl)-benzamide (Example 29d, 0.284 g), di-t-butyldicarbonate (0.284 g), triethylamine (0.2 ml) and dichloromethane (5 ml) were stirred together under nitrogen for 48 h, then poured into water and extracted into ethyl acetate. The combined extracts were dried over magnesium sulfate, filtered and concentrated under reduced pressure to afford the sub-title compound (0.330 g) as an oil.

MS (APCI+ve) 536/538 (M+H)+ b) [2-[[4-Chloro-3-[[(tricyclo[3.3.1.1$^{3,7}$]dec-1-ylmethyl)amino]carbonyl]phenyl]-amino]ethyl][2-(methylsulfinyl)ethyl]-carbamic acid, 1,1-dimethylethyl ester Prepared according to the method of Example 22 from [2-[[4-chloro-3-[[(tricyclo[3.3.1.1$^{3,7}$]dec-1-ylmethyl)amino]carbonyl]phenyl]amino]ethyl][2-(methylthio)ethyl]-carbamic acid, 1,1-dimethylethyl ester (0.460 g, Example 30a), 3-chloroperoxybenzoic acid (0.315 g) and dichloromethane (20 ml). Excess calcium hydroxide was added, followed by excess magnesium sulfate. The mixture was filtered through celite and concentrated under reduced pressure. The crude material was purified on silica gel (19:1/dichloromethane:methanol) to afford the sub-title compound as a gum (0.141 g) and the corresponding sulfone (0.057 g).

MS (APCI+ve) 552/554 (M+H)+ c) 2-Chloro-5-[[2-[[2-(methylsulfinyl)ethyl]amino]ethyl]amino]-N-(tricyclo[3.3.1.1$^{3,7}$]dec-1-ylmethyl)-benzamide, acetic acid salt

[2-[[4-Chloro-3-[[(tricyclo[3.3.1.1$^{3,7}$]dec-1-ylmethyl)amino]carbonyl]phenyl]-amino]ethyl][2-(methylsulfinyl)ethyl]-carbamic acid, 1,1-dimethylethyl ester (0.141 g, Example 30b), 4M hydrogen chloride in 1,4-dioxane (10 ml) and methanol (10 ml) were stirred together under nitrogen for 3 h. The mixture was poured into 25% aqueous ammonia solution and concentrated under reduced pressure to give the free base. This was purified by column chromatography over silica gel (eluting with 19:1:0.1/ dichloromethane:methanol:ammonia), and the resulting oil repurified by RPHPLC (eluant NH$_4$OAc: CH$_3$CN/75%:25% to 5%:95% gradient) to afford the title compound (0.030 g).

MS (APCI+ve) 4521454 (M+H)+

$^1$H NMR (CDCl$_3$) δ7.15 (1H, d); 6.96 (1H, m); 6.62–6.59 (1H, m); 6.36 (1H, br t); 3.23–3.07 (6H, m); 2.93–2.78 (4H, m); 2.62 (3H, s); 2.00 (3H, br s); 1.69 (6H, m); 1.58 (6H, s).

EXAMPLE 31

2-Chloro-5-[2-[(2-hydroxy-2-methylpropyl)amino]ethoxy]-N-(tricyclo[3.3.1.1$^{3,7}$]dec-1-ylmethyl)benzamide, dihydrochloride

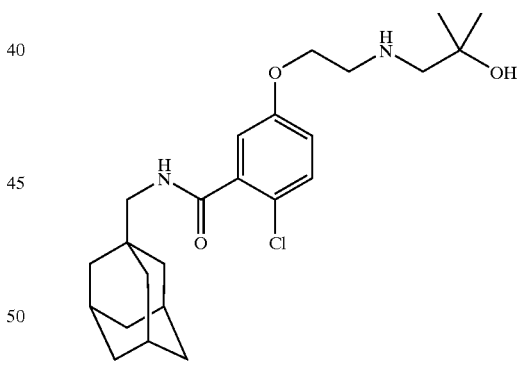

Prepared from 2-chloro-5-[2-[2-chloroethoxy]ethoxy]-N-(tricyclo[3.3.1.1$^{3,7}$]dec-1-ylmethyl)-benzamide (0.380 g, Example 28a) according to the procedure described in Example 28b to afford the title compound as a solid (0.038 g)

MS (APCI+ve) 435/437 (M+H)+

$^1$H NMR (d6-DMSO) δ8.71–8.40 (2H, m), 8.33 (1H t, J=6.2 Hz), 7.43 (1H, d, J=8.7), 7.05 (2H, dd, J 8.7,3.0 Hz), 6.99 (1H, d, J=3.1 Hz,), 5.21 (1H, S), 4.31 (2H, t, J=5.2 Hz), 3.46–3.23 (2H, m), 2.99 (3H, d, J=5.8 Hz), 2.93 (3H, d, J=6.3 Hz), 1.94 (3H, s), 1.63 (6H, m), 1.52 (s, 6H), 1.28 (s, 6H)

EXAMPLE 32

2-Chloro-5-[[2-[[2-(1-methyl-1H-imidazol-5-yl)ethyl]amino]ethyl]amino]-N-(tricyclo[3.3.1.1$^{3,7}$]dec-1-ylmethyl)-benzamide

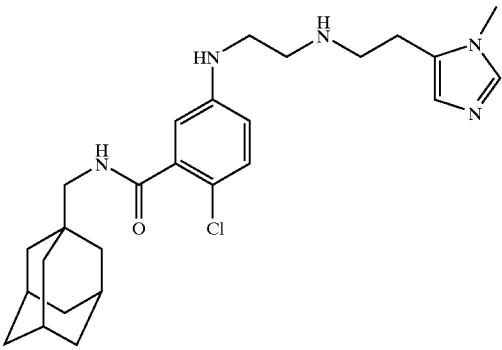

a) 2-Chloro-5-[[2-[[2-(1-methyl-1H-imidazol-5-yl)ethyl]amino]ethyl]amino]-N-(tricyclo[3.3.1.1$^{3,7}$]dec-1-ylmethyl)-benzamide 2-Chloro-5-[(2-chloroethyl)amino]-N-(tricyclo[3.3.1.1$^{3,7}$]dec-1-ylmethyl)-benzamide (Example 29c, 0.100 g), 3-methylhistamine (0.200 g), N,N-diisopropylethylamine (0.5 ml), potassium iodide (0.040 g) and n-butanol (4 ml) were heated together in a sealed tube at 110° C. for 24 h. The solution was cooled, poured into saturated aqueous sodium hydrogencarbonate solution and extracted into ethyl acetate. The extracts were dried over magnesium sulfate, filtered and concentrated under reduced pressure. The crude material was purified on silica gel (eluant 19:1:0.1 dichloromethane/methanol/ammonia) to afford the title compound as a gum (0.053 g).

MS (APCI+ve) 470/472 (M+H)$^+$ $^1$H NMR (CDCl$_3$) δ7.37 (1H, s); 7.15 (1H, d); 6.93–6.92 (1H, m); 6.75 (1H, s); 6.61–6.57 (2H, m); 4.31 (1H, br t); 3.56 (3H, s); 3.23–3.16 (4H, m); 2.89 (4H, t); 2.75 (2H, t); 2.00 (3H, br s); 1.69 (6H, m); 1.59 (6H, brs).

EXAMPLE 33

2-Chloro-5-[[2-[[2-(1-methyl-1H-imidazol-4-yl)ethyl]amino]ethyl]amino]-N-(tricyclo[3.3.1.1$^{3,7}$]dec-1-ylmethyl)-benzamide

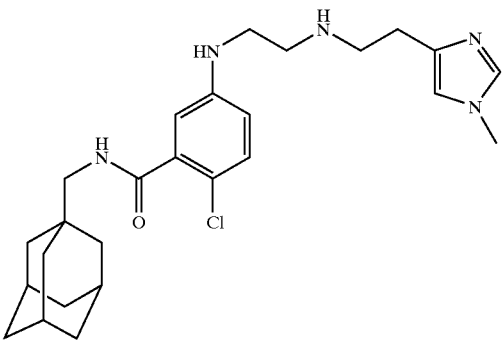

Prepared as in Example 32 using 2-chloro-5-[(2-chloroethyl)amino]-N-(tricyclo[3.3.1.1$^{3,7}$]dec-1-ylmethyl)-benzamide (Example 29c, 0.200 g), 1-methylhistamine (0.400 g), N,N-diisopropylethylamine (1 ml), potassium iodide (0.080 g) and n-butanol (4 ml) to give the title compound as a gum (0.040 g).

MS (APCI+ve) 470/472 (M+H)$^+$ $^1$H NMR (CDCl$_3$) δ7.34 (1H, s), 7.13 (1H, d); 6.94 (1H, d); 6.34 (1H s); 6.57 (1H, dd); 6.37 (1H, br t); 4.56 (1H, br t); 3.62 (3H, s); 3.20–3.15 (4H, m); 2.93–2.87 (4H, m); 2.73 (2H, t); 2.00 (3H, br s); 1.69 (6H, m); 1.58 (6H, s).

EXAMPLE 34

2-Chloro-5-[[2-[[3-(1H-imidazol-1-yl)propyl]amino]ethyl]amino]-N-(tricyclo[3.3.1.1$^{3,7}$]dec-1-ylmethyl)-benzamide

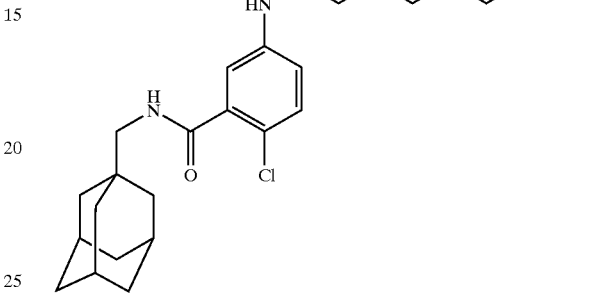

2-Chloro-5-[(2-chloroethyl)amino]-N-(tricyclo[3.3.1.1$^{3,7}$]dec-1-ylmethyl)-benzamide (Example 29c, 0.200 g), N-(3-aminopropyl)-imidazole (0.957 g), triethylamine (1.2 ml), sodium iodide (0.010 g) and tetrahydrofuran (4 ml) were heated together in a sealed tube at 80° C. for 24 h. The solution was cooled, poured into saturated aqueous sodium hydrogencarbonate solution and extracted into ethyl acetate. The extracts were dried over magnesium sulfate, filtered and concentrated under reduced pressure. The crude material was purified on silica gel (eluant 19:1:0.1 dichloromethane/methanol/ammonia) to afford the title compound as a gum (0.176 g).

MS (APCI+ve) 470/472 (M+H)$^+$ $^1$H NMR (d6-DMSO) δ8.18 (1H, t); 7.58 (1H, s); 7.14–7.10 (2H, m); 6.86 (1H, s); 6.60–6.57 (2H, m); 5.85 (1H, t); 4.00 (2H, t); 3.07–3.06 (2H, m); 2.90–2.89 (2H, m); 2.67–2.65 (2H, m); 2.46–2.43 (2H, m); 1.93 (3H, br s); 1.85–1.78 (2H, m); 1.64 (6H, br m); 1.51 (6H, br s).

Pharmacological Analysis

Certain compounds such as benzoylbenzoyl adenosine triphosphate (bbATP) are known to be agonists of the P2X$_7$ receptor, effecting the formation of pores in the plasma membrane (Drug Development Research (1996), 37(3), p.126). Consequently, when the receptor is activated using bbATP in the presence of ethidium bromide (a fluorescent DNA probe), an increase in the fluorescence of intracellular DNA-bound ethidium bromide is observed. The increase in fluorescence can be used as a measure of P2X$_7$ receptor activation and therefore to quantify the effect of a compound on the P2X$_7$ receptor.

In this manner, each of the title compounds of Examples 1 to 34 was tested for antagonist activity at the P2X$_7$ receptor. Thus, the test was performed in 96-well flat bottomed microtitre plates, the wells being filled with 250 μl of test solution comprising 200 μl of a suspension of THP-1 cells (2.5×10$^6$ cells/ml) containing 10$^{-4}$ M ethidium bromide, 25 μl of a high potassium buffer solution containing 10$^{-5}$M bbATP, and 25 μl of the high potassium buffer solution containing 3×10$^{-5}$ M test compound. The plate was covered with a plastics sheet and incubated at 37° C. for one hour. The plate was then read in a Perkin-Elmer fluorescent plate reader, excitation 520 in, emission 595 nm, slit widths: Ex 15 nm, Em 20 nm. For the purposes of comparison, bbATP (a P2X$_7$ receptor agonist) and pyridoxal 5-phosphate (a P2X$_7$ receptor antagonist) were used separately in the test as controls. From the readings obtained, a pIC$_{50}$ figure was calculated for each test compound, this figure being the negative logarithm of the concentration of test compound necessary to reduce the bbATP agonist activity by 50%. Each of the compounds of Examples 1 to 34 demonstrated antagonist activity, having a pIC$_{50}$ figure>5.0.

What is claimed is:

1. A compound of general formula

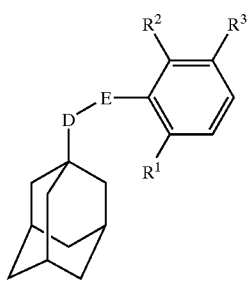

(I)

wherein D represents CH$_2$ or CH$_2$CH$_2$;

E represents C(O)NH or NHC(O);

R$^1$ and R$^2$ each independently represent a hydrogen or halogen atom, or an amino, nitro, C$_1$–C$_6$ alkyl or trifluoromethyl group;

R$^3$ represents a group of formula

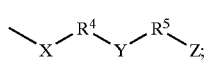

(II)

X represents an oxygen or sulphur atom or a group NH, SO or SO$_2$;

Y represents an oxygen or sulphur atom or a group NR$^{11}$, SO or SO$_2$;

Z represents a group —OH, —SH, —CO$_2$H, C$_1$–C$_6$ alkoxy, C$_1$–C$_6$ alkylthio, C$_1$–C$_6$-alkylsulphinyl, C$_1$–C$_6$-alkylsulphonyl, —NR$^6$R$^7$, —C(O)NR$^8$R$^9$, imidazolyl, 1-methylimidazolyl, —N(R$^{10}$)C(O)—C$_1$–C$_6$ alkyl, C$_1$–C$_6$ alkylcarbonyloxy, C$_1$–C$_6$ alkoxycarbonyloxy, —OC(O)NR$^{12}$ R$^{13}$, —OCH$_2$OC(O)R$^{14}$, —OCH$_2$OC(O)OR$^{15}$ or —OC(O)OCH$_2$OR$^6$;

R$^4$ represents a linear or branched C$_2$–C$_6$ alkylene group;

R$^5$ represents a linear or branched C$_1$–C$_6$ alkylene group;

R$^6$, R$^7$, R$^8$, R$^9$, R$^{10}$, R$^{12}$ and R$^{13}$ each independently represent a hydrogen atom, or a C$_1$–C$_6$ alkyl group optionally substituted by at least one hydroxyl group;

R$^{11}$ represents a hydrogen atom, or a C$_1$–C$_6$ alkyl group optionally substituted by at least one substituent independently selected from hydroxyl and C$_1$–C$_6$ alkoxy; and R$^{14}$, R$^{15}$ and R$^{16}$ each independently represent a C$_1$–C$_6$ alkyl group; with the provisos that (i) when E represents NHC(O), X represents O, S or NH and Y represents O, then Z represents —NR$^6$R$^7$ where R$^6$ represents a hydrogen atom and R$^7$ represents either a hydrogen atom or a C$_1$–C$_6$ alkyl group substituted by at least one hydroxyl group, and (ii) when E represents NHC(O), X represents O, S or NH, Y represents NH and R$^5$ represents CH$_2$CH$_2$, then Z is not —OH or imidazolyl; or a pharmaceutically acceptable salt or solvate thereof.

2. The compound according to claim 1, wherein D represents CH$_2$.

3. The compound according to claim 1, wherein E represents NHC(O).

4. The compound according to claim 1, wherein R$^1$ and R$^2$ each independently represent a hydrogen, chlorine or bromine atom, or an amino, nitro, C$_1$–C$_3$ alkyl or trifluoromethyl group.

5. The compound according to claim 1, wherein X represents an oxygen atom or a group NH.

6. The compound according to claim 1, wherein Y represents a group NR$^{11}$.

7. The compound according to claim 6, wherein R$^{11}$ represents a hydrogen atom.

8. The A compound according to claim 1, wherein Z represents a group —OH, —CO$_2$H, methoxy, methylthio, methylsulphinyl, methylsulphonyl, —NR$^6$ R$^7$, imidazolyl, 1-methylimidazolyl, —C(O)NR$^8$ R$^9$, —N(R$^{10}$)C(O)CH$_3$, C$_1$–C$_4$ alkylcarbonyloxy, C$_1$–C$_4$ alkoxycarbonyloxy, —OC(O)NR$^{12}$R$^{13}$, —OCH$_2$OC(O)R$^{14}$, —OCH$_2$OC(O)OR$^{15}$ or —OC(O)OCH$_2$OR$^{16}$.

9. The compound of formula (I), or pharmaceutically acceptable salt or solvate thereof, according to claim 1 which is selected from:

2-Chloro-5-[2-(2-methoxyethylamino)ethylamino]-N-(tricyclo[3.3.1.1$^{3,7}$]dec-1-ylmethyl)-benzamide, hydrochloride,

[2-[4-Chloro-3-(tricyclo[3.3.1.1$^{3,7}$]dec-1-ylmethyl) carbamoyl-phenylamino]-ethyamino]-acetic acid, hydrochloride, 2-Chloro-5-[3-(3-hydroxy-propylamino)-propoxy]-N-(tricyclo[3.3.1.1$^{3,7}$]dec-1-ylmethyl) -benzamide, hydrochloride, 2-Chloro-5-[2-(3-hydroxypropylamino)ethylamino]-N-(tricyclo[3.3.1.1$^{3,7}$]dec-1-ylmethyl) -benzamide, acetate, 5-[2-(2-Aminoethylamino)ethylamino]-2-chloro-N-(tricyclo[3.3.1.1$^{3,7}$]dec-1-ylmethyl) -benzamide, acetate, 5-[2-(2-Acetylaminoethylamino)ethylamino[-2-chloro-N-(tricyclo[3.3.1.1$^{3,7}$]dec-1-ylmethyl -benzamide, acetate,

[2-[4-Chloro-3-(tricyclo[3.3.1.1$^{3,7}$]dec-1-ylmethyl) carbamoyl-phenylamino]-ethylamino]-propionic acid, 2-Chloro-5-[2-(2-methylcarbamoylethylamino) ethylamino]-N-(tricyclo[3.3.1.1$^{3,7}$]dec-1-ylmethyl)-benzamide, acetate, 2-Chloro-5-[2-(2-dimethylcarbamoylethylamino) ethylamino]-N-(tricyclo[3.3.1.1$^{3,7}$]dec-1-ylmethyl)-benzamide, acetate, 2-Chloro-5-[3-(3-hydroxypropylthio)propoxy]-N-(tricyclo[3.3.1.1$^{3,7}$]dec-1-ylmethyl) -benzamide, 5-[2-(2-Aminoethylthio)ethoxy]-2-chloro-N-(tricyclo[3.3.1.1$^{3,7}$]dec-1-ylmethyl)-benzamide, hydrochloride, 2-Chloro-5-[2-(3-hydroxypropylamino)ethoxy]-N-(tricyclo[3.3.1.1$^{3,7}$]dec-1-ylmethyl) -benzamide, hydrochloride, 2-Chloro-5-[3-(3-hydroxypropylsulfonyl)propoxy]-N-(tricyclo[3.3.1.1$^{3,7}$]dec-1-ylmethyl) -benzamide, (±)-2-Chloro-5-[3-(3-hydroxypropylsulfinyl)propoxy]-N-(tricyclo[3.3.1.1$^{3,7}$]dec-1-ylmethyl)-benzamide, 2-Chloro-5-[2-(3-hydroxypropylthio)ethoxy]-N-(tricyclo[3.3.1.1 $^{3,7}$]dec-1-ylmethyl) -benzamide, (S)-2-Chloro-5-[2-(2-hydroxypropylamino)ethoxy]-N-(tricyclo[3.3.1.1$^{3,7}$]dec-1-ylmethyl) -benzamide, hydrochloride, (R)-2-Chloro-5-[2-(2-hydroxypropylamino)ethoxy]-N-(tricyclo[3.3.1.1³,⁷]dec-1-ylmethyl) -benzamide, hydrochloride, (S)-2-Chloro-5-[2-(2-hydroxy-1-methylethylamino) ethoxy]-N-(tricyclo[3.3.1.1³,⁷]dec-1-ylmethyl)-benzamide, hydrochloride, (R)-2-Chloro-5-[2-(2-hydroxy-1-methylethylamino) ethoxy]-N-(tricyclo[3.3.1.1³,⁷]dec-1-ylmethyl)-benzamide, hydrochloride, (±)-2-Chloro-5-[2-(3-hydroxypropylsulfinyl)ethoxy]-N-(tricyclo[3.3.1.1³,⁷]dec-1-ylmethyl)-benzamide, 2-Chloro-5-[2-(3-hydroxypropylsulfonyl)ethoxy]-N-(tricyclo[3.3.1.1³,⁷]dec-1-ylmethyl) -benzamide, (±)-5-[2-(2-Aminoethylsulfinyl)ethoxy]-2-chloro-N-(tricyclo[3.3.1.1³,⁷]dec-1-ylmethyl) -benzamide, hydrochloride, 5-[2-(2-Aminoethylsulfonyl)ethoxy]-2-chloro-N-(tricyclo[3.3.1.1³,⁷]dec-1-ylmethyl) -benzamide, hydrochloride, 5-[3-(2-Aminoethylthio)propoxy]-2-chloro-N-(tricyclo[3.3.1.1³,⁷]dec-1-ylmethyl) -benzamide, hydrochloride, (±)-5-[3-(2-Aminoethylsulfinyl)propoxy]-2-chloro-N-(tricyclo[3.3.1.1³,⁷]dec-1-ylmethyl) -benzamide, hydrochloride, 5-[3-(2-Aminoethylsulfonyl)propoxy]-2-chloro-N-(tricyclo[3.3.1.1³,⁷]dec-1-ylmethyl) -benzamide, hydrochloride, 2-Chloro-5-[[2-[(3-hydroxy-3-methylbutyl)amino]ethyl]amino]-N-(tricyclo[3.3.1.1³,⁷]dec-1-ylmethyl)-benzamide, 2-Chloro-5-[2-[2-[(2-hydroxyethyl)amino]ethoxy]ethoxy]-N-(tricyclo[3.3.1.1³,⁷]dec-1ylmethyl)-benzamide, hydrochloride, 2-Chloro-5-[[2-[[2-(methylthio)ethyl]amino]ethyl]amino]-N-(tricyclo[3.3.1.1³,⁷]dec-1ylmethyl)-benzamide, 2-Chloro-5-[[2-[[2-(methylsulfinyl)ethyl]amino]ethyl]amino]-N-(tricyclo[3.3.1.1³,⁷]dec-1-ylmethyl)-benzamide, acetic acid salt, 2-Chloro-5-[2-[(2-hydroxy-2-methylpropyl)amino]ethoxy]-N-(tricyclo[3.3.1.1³,⁷]dec-1-ylmethyl)benzamide, dihydrochioride, 2-Chloro-5-[[2-[[2-(1-methyl-1H-imidazol-5-yl)ethyl]amino]ethyl]amino]-N-(tricyclo[3.3.1.1 3³,⁷]dec-1-ylmethyl)-benzamide, 2-Chloro-5-[[2-[[2-(1-methyl-1H-imidazol-4-yl)ethyl]amino]ethyl]amino]-N-(tricyclo[3.3.1.1³,⁷]dec-1-ylmethyl)-benzamide, and 2-Chloro-5-[[2-[[3-(1H-imidazol-1-yl)propyl]amino]ethyl]amino]-N-(tricyclo[3.3.1.1³,⁷]dec-1-ylmethyl)-benzamide.

10. A process for the preparation of a compound of formula (I) as defined in claim 1 which comprises:

a) when Y represents an oxygen or sulphur atom or a group NR¹¹, reacting a compound of general formula

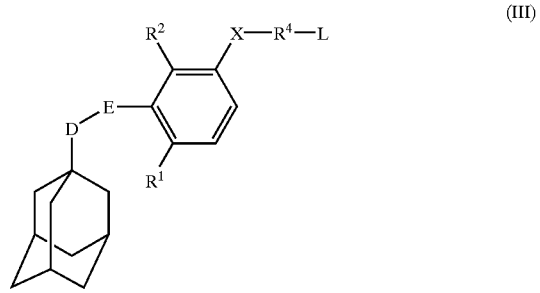

(III)

wherein L represents a leaving group and D, E, R¹, R², X and R⁴ are as defined in formula (I), with a compound of general formula

$R^{20}$—$R^5$—Z        (IV)

wherein $R^{20}$ represents —OH, —SH or —$NHR^{11}$ and $R^5$, $R^{11}$ and Z are as defined in formula (I); or b) when Y represents SO or $SO_2$, reacting a corresponding compound of formula (I) in which Y represents a sulphur atom with a suitable oxidising agent;

and optionally after (a) or (b) converting the compound of formula (I) obtained to a pharmaceutically acceptable salt or solvate thereof.

11. A pharmaceutical composition comprising a compound of formula (I), or a pharmaceutically acceptable salt or solvate thereof, as claimed in any one of claims 1 to 9 in association with a pharmaceutically acceptable adjuvant, diluent or carrier.

12. A process for the preparation of a pharmaceutical composition as claimed in claim 11 which comprises mixing said compound of formula (I), or pharmaceutically acceptable salt or solvate thereof, with a pharmaceutically acceptable adjuvant, diluent or carrier.

13. A method of effecting immunosuppression which comprises administering a therapeutically effective amount of a compound of formula (I), or a pharmaceutically acceptable salt or solvate thereof, as claimed in any one of claims 1 to 9 to a patient in need thereof.

14. A method of treating rheumatoid arthritis which comprises administering a therapeutically effective amount of a compound of formula (I), or a pharmaceutically acceptable salt or solvate thereof, as claimed in any one of claims 1 to 9 to a patient in need thereof.

15. A method of treating chronic obstructive pulmonary disease which comprises administering a therapeutically effective amount of a compound of formula (I), or a pharmaceutically acceptable salt or solvate thereof, as claimed in any one of claims 1 to 9 to a patient in need thereof.

* * * * *